United States Patent
Etzkorn

(10) Patent No.: US 8,960,899 B2
(45) Date of Patent: Feb. 24, 2015

(54) ASSEMBLING THIN SILICON CHIPS ON A CONTACT LENS

(71) Applicant: Google Inc., Mountain View, CA (US)

(72) Inventor: James Etzkorn, Mountain View, CA (US)

(73) Assignee: Google Inc., Mountain View, CA (US)

( * ) Notice: Subject to any disclaimer, the term of this patent is extended or adjusted under 35 U.S.C. 154(b) by 28 days.

(21) Appl. No.: 13/627,574

(22) Filed: Sep. 26, 2012

(65) Prior Publication Data

US 2014/0084489 A1    Mar. 27, 2014

(51) Int. Cl.
| | | |
|---|---|---|
| G02C 7/02 | (2006.01) | |
| H01L 23/48 | (2006.01) | |
| H01L 21/56 | (2006.01) | |
| G02C 7/04 | (2006.01) | |
| H01L 23/00 | (2006.01) | |

(52) U.S. Cl.
CPC .............. *H01L 23/48* (2013.01); *H01L 21/563* (2013.01); *G02C 7/049* (2013.01); *H01L 24/97* (2013.01); *H01L 2924/10253* (2013.01)
USPC ................. 351/159.03; 351/159.39

(58) Field of Classification Search
CPC ................. H01L 2924/00; H01L 2224/48227; H01L 27/14618; H01L 33/08; H01L 27/14627
USPC .............................. 351/159, 160 R
See application file for complete search history.

(56) References Cited

U.S. PATENT DOCUMENTS

| | | |
|---|---|---|
| 3,958,560 A | 5/1976 | March |
| 4,014,321 A | 3/1977 | March |
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |

(Continued)

FOREIGN PATENT DOCUMENTS

| | | |
|---|---|---|
| EP | 0369942 | 5/1990 |
| EP | 686372 | 12/1995 |

(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

(Continued)

*Primary Examiner* — Matthew W Such
*Assistant Examiner* — Ali Naraghi
(74) *Attorney, Agent, or Firm* — McDonnell Boehnen Hulbert & Berghoff LLP

(57) ABSTRACT

A contact lens having a thin silicon chip integrated therein is provided along with methods for assembling the silicon chip within the contact lens. In an aspect, a method includes creating a plurality of lens contact pads on a lens substrate and creating a plurality of chip contact pads on a chip. The method further involves applying assembly bonding material to the each of the plurality of lens contact pads or chip contact pads, aligning the plurality of lens contact pads with the plurality of chip contact pads, bonding the chip to the lens substrate via the assembly bonding material using flip chip bonding, and forming a contact lens with the lens substrate.

21 Claims, 15 Drawing Sheets

(56) References Cited

U.S. PATENT DOCUMENTS

| | | |
|---|---|---|
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint |
| 5,177,165 A | 1/1993 | Valint et al. |
| 5,177,168 A | 1/1993 | Baron |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,134,736 A | 10/2000 | Pankow |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2006/0254369 A1* | 11/2006 | Yoon et al. ............ 73/862.041 |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0103368 A1* | 4/2010 | Amirparviz et al. ......... 351/158 |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0254158 A1* | 10/2011 | Kaylani et al. ................ 257/737 |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0074598 A1* | 3/2012 | Kalz .............................. 257/788 |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |

(56) References Cited

U.S. PATENT DOCUMENTS

| | | | |
|---|---|---|---|
| 2012/0109296 A1 | 5/2012 | Fan | |
| 2012/0177576 A1 | 7/2012 | Hu | |
| 2012/0201755 A1 | 8/2012 | Rozakis et al. | |
| 2012/0206691 A1 | 8/2012 | Iwai | |
| 2012/0245444 A1 | 9/2012 | Otis et al. | |
| 2012/0259188 A1* | 10/2012 | Besling | 600/319 |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |
| EP | 2457122 | 5/2012 |
| JP | 2003-195230 | 7/2003 |
| WO | 9504609 | 2/1995 |
| WO | 0116641 | 3/2001 |
| WO | 0134312 | 5/2001 |
| WO | 03065876 | 8/2003 |
| WO | 2004060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gent Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'to project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Selner, et al., "Novel Contact Lens Electrode Array for Multi-electrode Electroretinography (meERG)," IEEE, 2011, 2 pages.

Liao, et al., "A 3-μW CMOS Glucose Sensor for Wireless Contact-Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions on Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Liao, et al., "A 3μW Wirelessly Powered CMOS Glucose Sensor for an Active Contact Lens," 2011 IEEE International Solid-State Circuits Conference, Session 2, Feb. 21, 2011, 3 pages.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

(56) References Cited

OTHER PUBLICATIONS

Lončar, et al., "Design and Fabrication of Silicon Photonic Crystal Optical Waveguides," Journal of Lightwave Technology, Oct. 2000, vol. 18, No. 10, pp. 1402-1411.
Liu, et al., "Miniature Amperometric Self-Powered Continuous Glucose Sensor with Linear Response," Analytical Chemistry, 7 pages.
Baxter, "Capacitive Sensors," 2000, 17 pages.
Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyvinylidene_fluoride, Last accessed Mar. 30, 2012, 4 pages.
Murdan, "Electro-responsive drug delivery from hydrogels," Journal of Controlled Release, 2003, vol. 92, pp. 1-17.
Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
Unpublished U.S. Appl. No. 13/240,994, Titled "See-Through Display With Infrared Eye-Tracker," filed Sep. 22, 2011, 38 pages.
Unpublished U.S. Appl. No. 13/209,706, Titled "Optical Display System and Method with Gaze Tracking," filed Aug. 15, 2011, 30 pages.
Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.
Bull, "Different Types of Statistical Analysis," Article Click, Feb. 4, 2008, 4 pages, http://www.articleclick.com/Article/Different-Types-Of-Statistical-Analysis/968252, Last accessed Sep. 4, 2012.
"Understanding pH measurement," Sensorland, 8 pages, http://www.sensorland.com/HowPage037.html, Last accessed Sep. 6, 2012.
"Regression analysis," Wikipedia, 11 pages, http://en.wikipedia.org/wiki/Regression_analysis, Last accessed Sep. 6, 2012.
"Statistics," Wikipedia, 10 pages, http://en.wikipedia.org/wiki/Statistics, Last accessed Sep. 6, 2012.
"Nonlinear regression," Wikipedia, 4 pages, http://en.wikipedia.org/wiki/Nonlinear_regression, Last accessed Sep. 10, 2012.
"Linear regression," Wikipedia, 15 pages, http://en.wikipedia.org/wiki/Linear_regression, Last accessed Sep. 10, 2012.
"Integrated circuit," Wikipedia, 9 pages, http://en.wikipedia.org/wiki/Integrated_circuit, Last accessed Sep. 10, 2012.
"Photolithography," Wikipedia, 8 pages, http://en.wikipedia.org/wiki/Photolithography, Last accessed Sep. 10, 2012.
"Alcohol Detection Technologies: Present and Future," American Beverage Institute, 9 pages.
Harding, et al., "Alcohol Toxicology for Prosecutors: Targeting Hardcore Impaired Drivers," American Prosecutors Research Institute, Jul. 2003, 40 pages.
Kim, et al., "Oral Alcohol Administration Disturbs Tear Film and Ocular Surface," American Academy of Ophthalmology, 2012, 7 pages.
Quick, "Color-changing electrochromic lens technology has fashion and military applications," Gizmag, Jul. 12, 2011, http://www.gizmag.com/electrochromic-lens-technology/19191/, Last accessed Apr. 12, 2012, 4 pages.
Chu, "Contact Lenses that Respond to Light," Technology Review, Nov. 10, 2009, http://www.technologyreview.com/printer_friendly_article.aspx?id=23922, Last accessed Apr. 12, 2012, 2 pages.
International Searching Authority, International Search Report and Written Opinion for PCT/US2013/059256 mailed Dec. 10, 2013, 10 pages.

\* cited by examiner

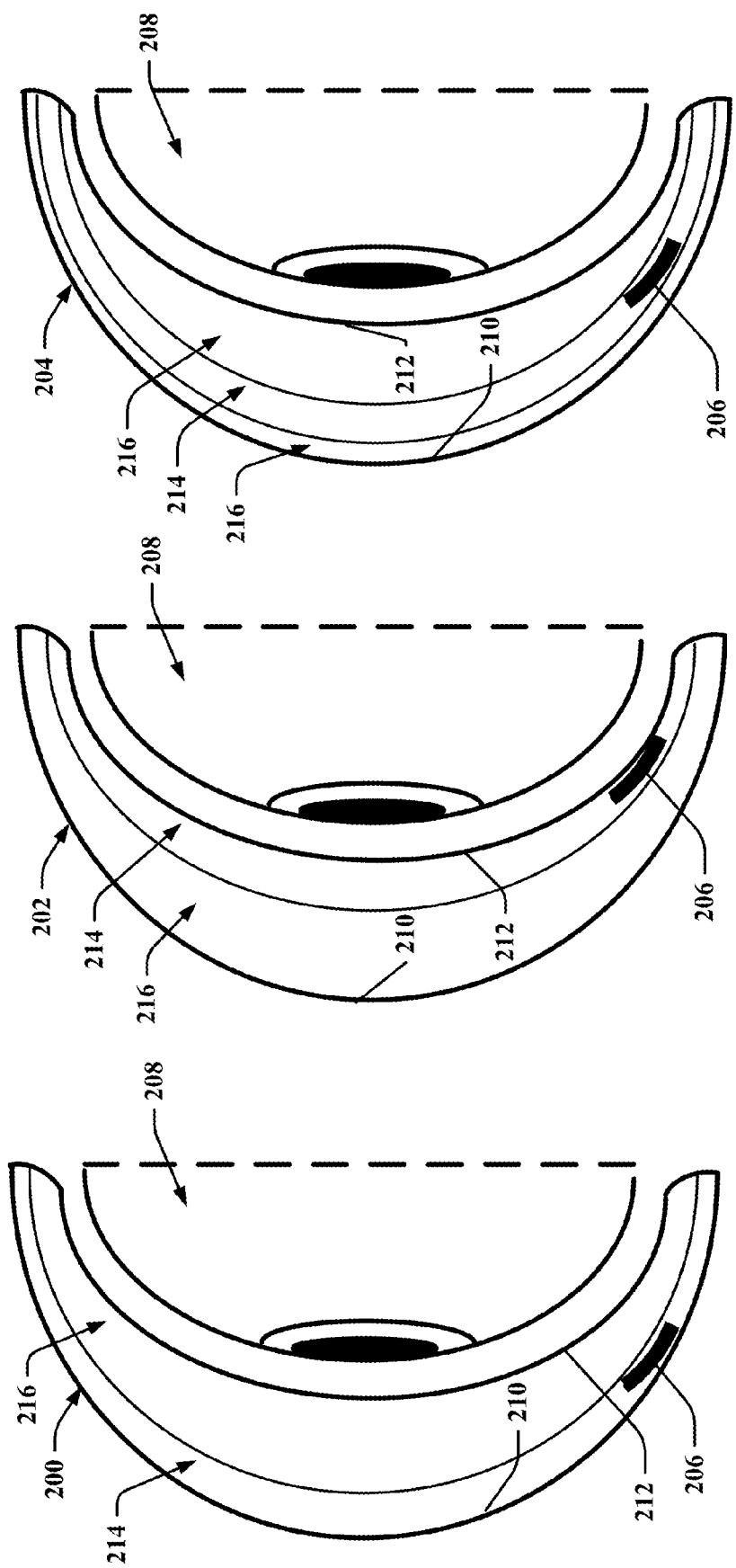

… (1)

ASSEMBLING THIN SILICON CHIPS ON A CONTACT LENS

TECHNICAL FIELD

This disclosure generally relates to a contact lens having a thin silicon chip integrated therein and methods for assembling the silicon chip within the contact lens.

BACKGROUND

Silicon chips are generally assembled using flip chip bonding or wire bonding. Flip chip bonding is a method for interconnecting semiconductor devices to external circuitry (e.g., a circuit board or another chip or wafer), with solder bumps that have been deposited onto chip pads. The solder bumps are deposited on the chip pads on a top side of the wafer during a final wafer processing step. In order to mount the chip to external circuitry it is flipped over so that its top side faces down, and aligned so that its pads align with matching pads on an external circuit. The solder bumps are then melted to complete interconnects. In wire bonding, the chip is mounted to external circuitry in an upright position and wires are used to interconnect the chip pads to external circuitry. However, these silicon chip assembly methods are not suitable for assembling silicon chips on or within a contact lens. Furthermore, standard chips are too thick to fit onto a contact lens.

BRIEF DESCRIPTION OF THE DRAWINGS

FIGS. 2A-2C present cross-sectional views of example embodiments of a contact lens having a silicon chip integrated therein in accordance with aspects described herein.

DETAILED DESCRIPTION

Figure 1B:
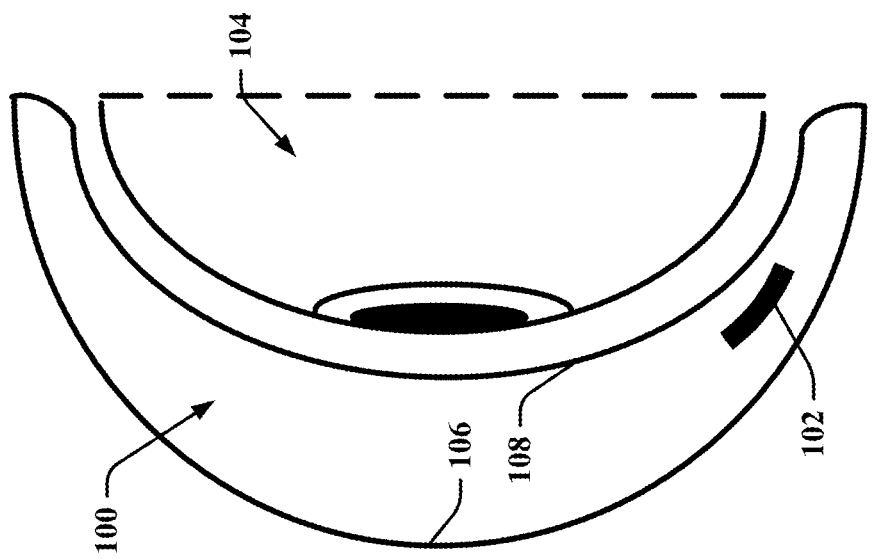
FIGS. 1A and 1B present alternative perspectives of an example contact lens having a silicon chip integrated therein/thereon in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

In one or more aspects, the disclosed subject matter relates to methods for manufacturing a contact lens having an integrated circuit integrated therein or thereon. In an aspect, the method involves creating a plurality of lens contact pads on a lens substrate and creating a plurality of chip contact pads on an integrated circuit element or chip, such as a silicon chip. Assembly bonding material is then applied to the plurality of lens contact pads or the plurality of chip contact pads. The chip is then bonded to the lens substrate via the assembly bonding material whereby the lens contact pads are aligned with the chip contact pads.

After the chip is bonded to the lens substrate, the lens substrate is formed into a contact lens. In an aspect, prior to forming the lens substrate into a contact lens, the chip is sealed onto the lens substrate. The lens substrate is then cut into a ring shape and molded to match curvature of an eye over which the contact lens is to be worn. The molded lens substrate is then embedded into a hydrogel to form the contact lens.

In some aspects, the plurality of chip contact pads are formed as metal lines on the chip using photolithography. Similarly, the plurality of lens contact pads can be formed as metal lines on the lens substrate using photolithography. Yet in other aspects, the plurality of lens contact pads are formed as a plurality of metal squares having a length of about 100 microns or less.

The subject methods enable assembly of thin silicon chips within a contact lens without use of bumped pads and standard chips. In some embodiments, the disclosed methods involve thinning a silicon ship substrate down to a thickness of less than about 100 microns (e.g., within the range of 20-100 microns thick) and then dicing the thinned substrate into chips smaller than 1 mm on each side. It is to be appreciated that these noted ranges/sizes are merely exemplary, and any suitable thickness or size can be employed in accordance with embodiments described herein. Metal lines are patterned onto a chip and/or a lens substrate to create contact pads for the chip and/or the lens substrate. The metal lines also serve as wires to connect other chips and/or other electrical components of the contact lens (e.g. antennas, sensors, light illuminating diodes (LEDS), and etc.).

In various embodiments, in order to assemble a chip to the lens substrate, a small amount of low temperature assembly bonding material is placed onto contact pads of either the lens substrate or the chip using a syringe. The contact pads of the chip are then aligned with the contact pads of the lens substrate and the chip is bonded to the lens substrate using the solder material. For example, the lens substrate can include multiple contact pads that can be segmented into multiple assembly sites for assembling a chip thereto. Once respective contact pads of a particular assembly site on the lens substrate are covered with solder material, the contact pads of the chip are aligned with the lens substrate contact pads in the assembly site and the chip is bonded to the assembly site using a flip-chip bonder. The flip-chip bonder tool aligns the chip contact pads with the lens substrate contact pads and applies pressure along with temperature to create a mechanical and electrical connection between the chip and the lens substrate.

After the chip is bonded to the lens substrate, the chip can be sealed onto the lens substrate with a substance (e.g. parylene) to make the lens substrate biocompatible and to hold the chip in place. The lens substrate can then be formed into a contact lens. For example, in an aspect, the lens substrate is cut into a ring shape. The ring shape can include indentations on the inner and/or outer edges of the ring to facilitate molding of the ring and to reduce wrinkling. The ring is then molded to match curvature of the eye. The ring is further embedded into hydrogel to complete the contact lens assembly process.

Figure 1A:
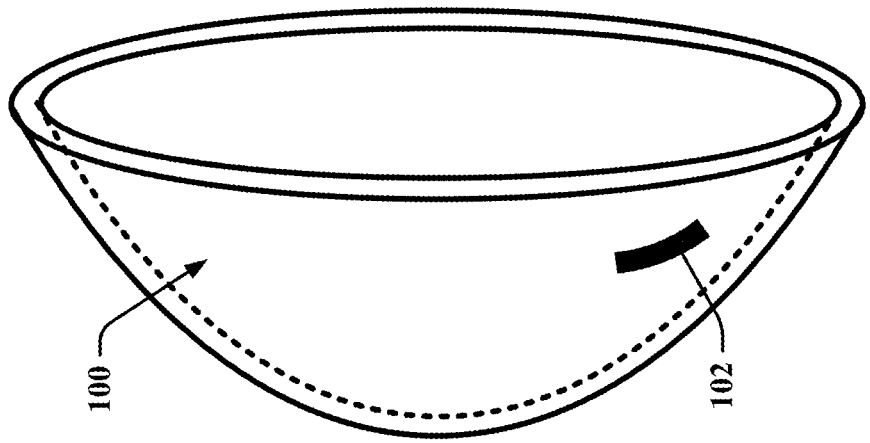

FIGS. 1A and 1B depict various perspectives of an example contact lens 100 having an integrated circuit or chip 102 integrated therein/thereon. As used herein, the terms integrated circuit and chip are used interchangeably. FIG. 1A illustrates a three dimensional image of example contact lens 100, and FIG. 1B presents a cross-sectional view of example contact lens 100 being worn over an eye 104. Contact lens 100, and additional contact lenses disclosed herein are generally provided in a spherical shape that conforms to shape of an eye.

With reference to FIG. 1B, contact lens 100 includes two primary surfaces, an inner surface 108 and an outer surface 106, both of which are spherical. The inner surface 108 is concave and is adjacent to/rests on, a surface of the eye 104. The outer surface 106 is convex and opposite the inner surface 108. The contact lens 100 has a thickness that spans in a horizontal direction between inner surface 106 and outer surface 104. Chip 102 is located within a thickness of the contact lens 102. In general aspects, as illustrated in FIG. 1B the width of the lens is thickest (relative to the width of the lens at other areas of the lens) at a center point of the lens, tapering outwardly to a knifelike edge at the perimeter of the lens. The particular dimensions (including dimensions attributable to thickness, diameter, curvature, and etc.) of the subject contact lenses are not critical and may vary.

As generally described herein, chip 102 is silicon chip that can be employed by contact lens 100 to facilitate electrical operations of the contact lens. In particular, chip 102 can perform various computing and logic functions of contact lens 102. Further, although not shorn in the figures, it is to be appreciated that contact lenses disclosed herein can include multiple electrical components that connect to silicon chip 102. For example, contact lenses disclosed herein can include sensors, antennas, LEDs, power sources, and etc. In addition, although contact lens 100 (and additional contact lenses described herein) is depicted having a single silicon chip 102, it should be appreciated than contact lens 100 (and additional contact lenses described herein) can be provided having a plurality of chips 102 integrated therein.

In an embodiment, silicon chip 102 is a piece of almost pure silicon having a size smaller than standard silicon chips employed in standard computing devices. For example, while most computing devices employ silicon chips that are one square centimeter and have a thickness of about 1 millimeter, chip 102 can have a size of about 1 square millimeter and a thickness less than 100 microns. In an aspect, silicon chip 102 contains a plurality (up to millions) of transistors and other small electronic circuit components, packed and interconnected in layers beneath the surface of the chip. The surface of the silicon chip can further include a grid of metallic lines etched thereon which are used to make electrical connections to other components of the chip 102 and/or the contact lens 100

FIGS. 2A-2C present cross-sectional views of example embodiments of a contact lens having silicon chip 206 integrated therein in accordance with aspects described herein. The contact lenses depicted in FIGS. 2A, 2B, and 2C, lenses 200, 202, and 204 respectively, respectively have two or more layers where silicon chip 206 is integrated within one of the layers. The lenses 200, 202, and 204 are formed by first integrating silicon chip 206 into a lens substrate layer 214 and then forming one or more additional contact lens layers 216 on and/or around the lens substrate layer 214. In particular, as described in detail infra, chip 206 is first assembled onto a lens substrate 214. In an aspect, the lens substrate is then molded into a lens shape to fit the contours of the eye 208 and combined within a contact lens material (e.g. hydrogel) to form the contact lens.

The lens substrate layer 214 having the silicon chip 206 and the contact lens material layer 216 can be combined in a variety of manners. In an aspect, in order to combine the lens substrate layer 214 and the contact lens material layer 216, the lens substrate can be dipped into liquid contact lens material 216. In another aspect, in order to combine the lens substrate layer 214 and the contact lens material layer 216, the lens substrate 214 can be coated/covered with lens contact material 216 on one or both sides of the lens substrate. Still in other aspects, in order to combine the lens substrate layer 214 and the contact lens material layer 216, the lens substrate 214 can be pressed into and/or bonded with one or more layers of lens contact material 216.

The lens substrate layer 214 and the lens material layer(s) 216 can include various materials. In an aspect, the lens substrate layer 214 and the lens material layer 216 comprise the same material. In another aspect, the lens substrate layer 214 and the lens material layer comprise different materials. The lens substrate layer 214 can include any suitable material that enables fixation of contact pads to the material (e.g. metal pads and/or metal lines) and fixation of a chip 206 to the contact pads.

Some exemplary material that can be employed as the lens substrate layer material 214 include but are not limited to a soft polymer material including but not limited to, a hydrogel, a silicone based hydrogel, a polyacrlyamide, or a hydrophilic polymer. For example, in an aspect, contact lens substrate layer 214 is formed from a substrate material that includes at least one of a crosslinked hydrogel comprising hydrophilic monomers (e.g. N-Vinylpyrrolidone, 1-Ethenyl-2-pyrrolidone,N,N-dimethylacrylamide, 2-hydroxyethyl methacrylate, hydroxyethyl acrylate, methacrylic acid and acrylic acid), a strengthening agent, a ultraviolet light (UV) blocker, or a tint.

In another aspect, contact lens substrate layer 214 is formed from a substrate material that includes at least of a one silicone hydrogel (e.g. crosslinked hydrogels containing silicone macromers and monomers, as well as hydrophilic monomers that absorb water). In yet another aspect, contact lens substrate layer 214 is formed from a substrate material that includes one or more rigid materials including but not limited to, a silicone polymer, polymethyl methacrylate, or rigid gas permeable materials.

The lens material layer 216 can include any suitable material that provides support for the lens substrate layer 214, contain/embed the lens substrate layer 214 and/or otherwise form a structural and/or functional body of the contact lens. Some exemplary materials that can be employed as the lens material layer 216 can include but are not limited to a soft polymer material including but not limited to, a hydrogel, a silicone based hydrogel, a polyacrlyamide, or a hydrophilic polymer. For example, in an aspect, lens material layer 216 is formed from a substrate material that includes at least one of a crosslinked hydrogel comprising hydrophilic monomers (e.g. N-Vinylpyrrolidone, 1-Ethenyl-2-pyrrolidone,N,N-dimethylacrylamide, 2-hydroxyethyl methacrylate, hydroxyethyl acrylate, methacrylic acid and acrylic acid), a strengthening agent, a ultraviolet light (UV) blocker, or a tint. In another aspect, lens material layer 216 is formed from a substrate material that includes at least of a one silicone hydrogel (e.g. crosslinked hydrogels containing silicone macromers and monomers, as well as hydrophilic monomers that absorb water). In yet another aspect, lens material layer 216 is formed from a substrate material that includes one or more rigid materials including but not limited to, a silicone polymer, polymethyl methacrylate, or rigid gas permeable materials.

As illustrated in FIG. 2A, in an aspect, the lens substrate layer 214 is located at an outer surface 210 of the contact lens 200 and the lens material layer 216 is located at an inner surface 212 of the contact lens 200. According to this aspect, contact lens 200 can include two layers, lens substrate layer 214 and a lens material layer 216. The lens substrate layer 214 includes the silicon chip and the silicon chip can further be located at/on the outer surface 210 of the contact lens. In an example, in order to form contact lens 200, silicon chip 206 is first integrated onto lens substrate layer 214 and then the lens substrate layer 214 is coated on its concave side with contact lens material 216.

As shown in FIG. 2B, in another aspect, the lens substrate layer 214 is located at an inner surface 212 of contact lens 202 and the lens material layer 216 is located at an outer surface 210 of the contact lens 202. According to this aspect, contact lens 202 can also include two layers, lens substrate layer 214 and a lens material layer 216. The lens substrate layer 214 includes the silicon chip 206 and the silicon chip can further be located at/on the inner surface 212 of the contact lens 202. In an example, in order to form contact lens 202, silicon chip 206 is first integrated onto lens substrate layer 214 and then the lens substrate layer 214 is coated on its convex side with contact lens material 216.

As seen in FIG. 2C, in yet another aspect, contact lens 204 includes a lens substrate layer 214 located between two layers of lens material 216. According to this aspect, contact lens 204 can also include three layers. The lens substrate layer 214 includes the silicon chip 206 and thus the silicon chip is located suspended between the inner surface 212 and the outer surface 210 of the contact lens 204. In an example, in order to form contact lens 204, silicon chip 206 is first integrated onto lens substrate layer 214 and then the lens substrate layer 214 is dipped into or otherwise entirely coated/embedded within, contact lens material 216.

Figure 3:
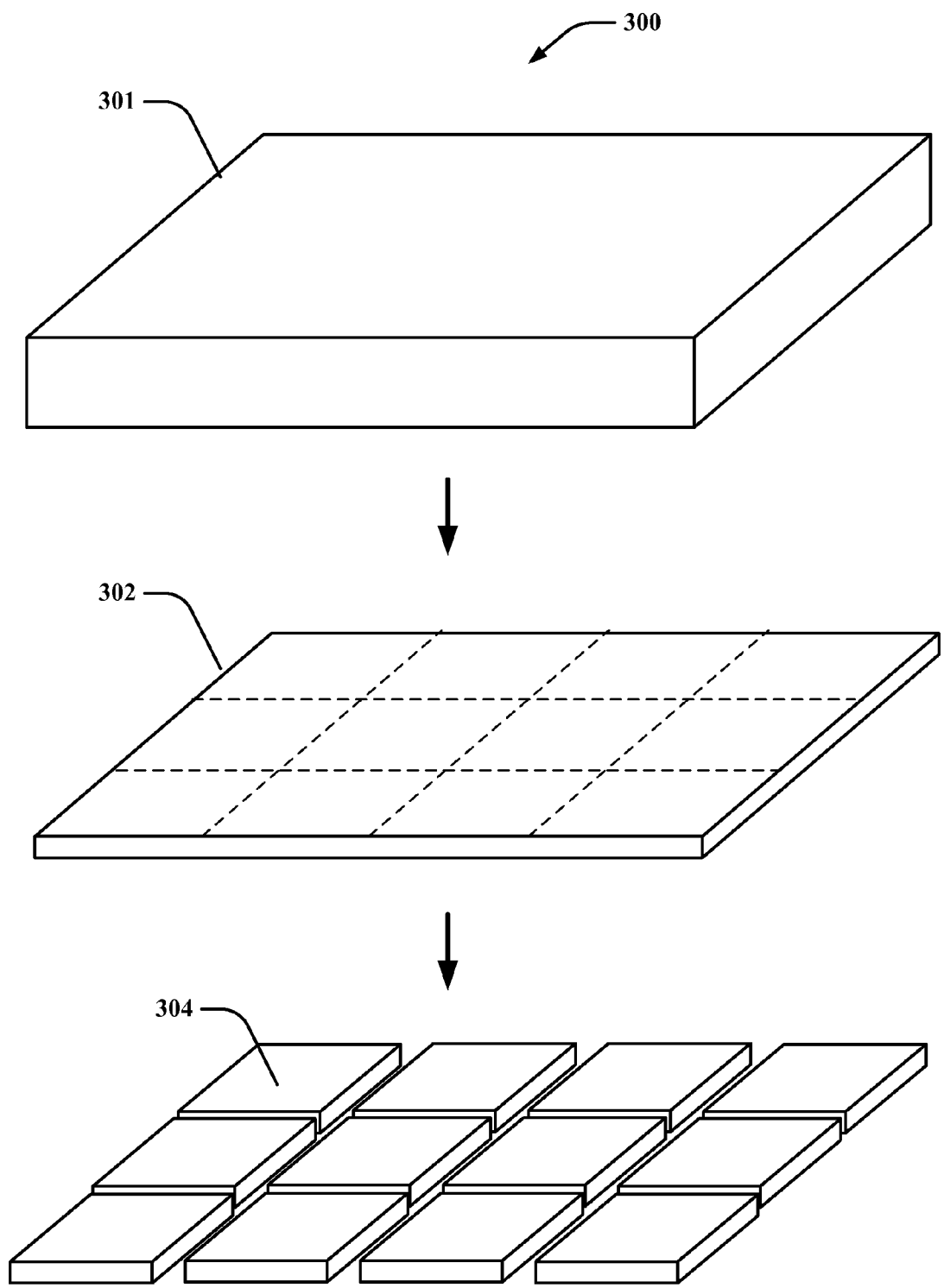
FIG. 3 depicts a process for creating silicon chips that can be assembled onto a contact lens in accordance with aspects described herein.

With reference now to FIG. 3, illustrated is a process 300 for creating silicon chips that can be assembled onto a contact lens in accordance with aspects described herein. A silicon chip substrate 301 is first thinned down to a thickness of less than 100 microns. In an aspect, the silicon chip substrate 301 is thinned down to a thickness of less than 75 microns. In another aspect, the silicon chip substrate 301 is thinned down to a thickness of less than 50 microns. Still, in yet another aspect, the silicon chip substrate 301 is thinned down to a thickness of less than 35 microns. The thinned silicon chip substrate 302 is then diced into a plurality of silicon chips 304 having a size suitable for integration into a contact lens. In particular, the size and shape of the chip 304 is restricted by thickness and curvature of a contact lens in which it is to be integrated. A chip 304 can have a rectangular shape or a square shape. In an aspect, a chip 304 can have sides less than 15 mm. In another aspect, a chip 304 can have sides less than 10 mm. In another aspect, a chip 304 can have sides less than 5.0 mm. Still in yet another aspect, a chip 304 can have sides less than 1.0 mm.

Figure 4:
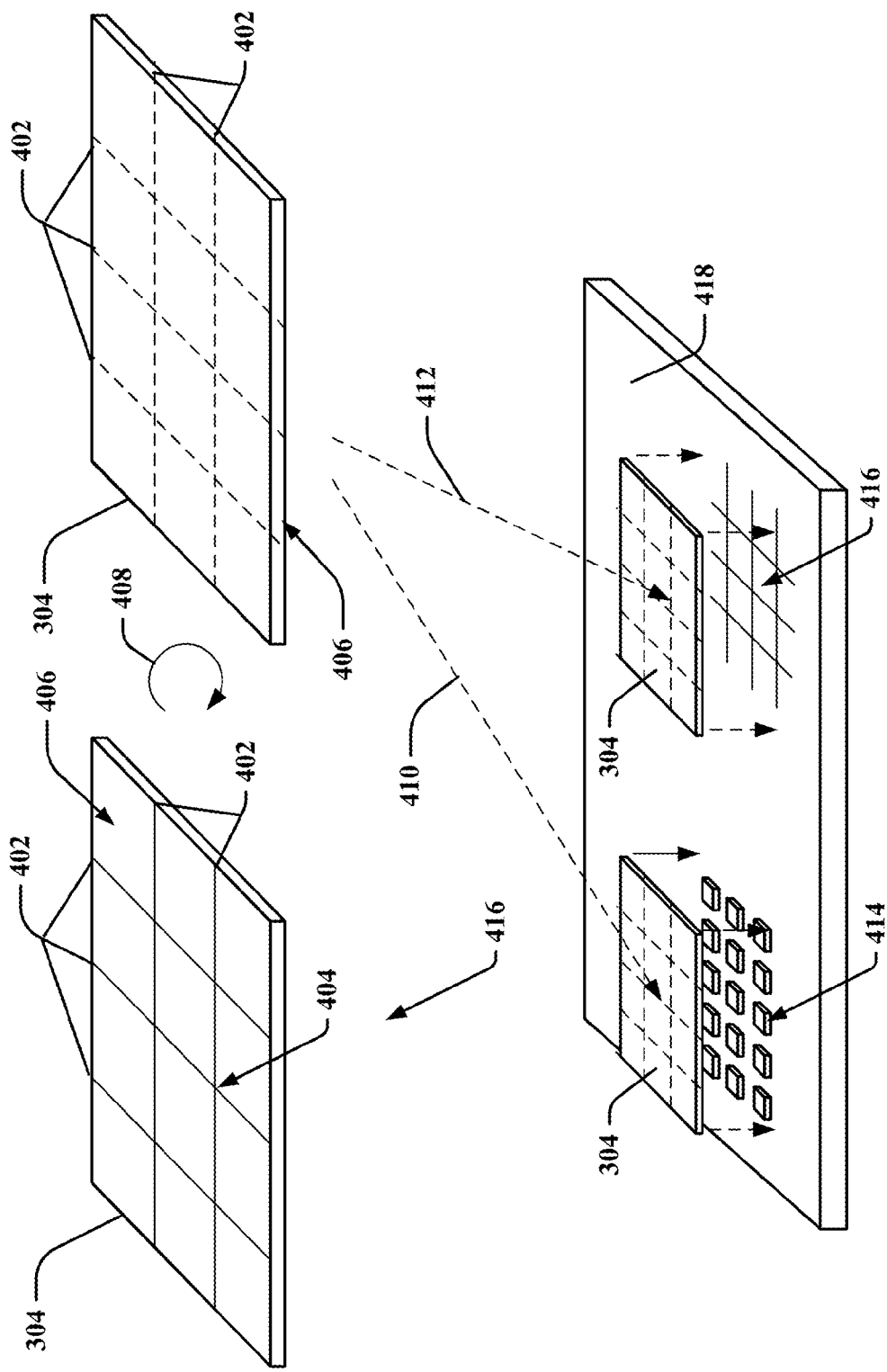
FIG. 4 illustrates a high level overview of processes by which a silicon chip is assembled onto a contact lens substrate in accordance with aspects described herein.

FIGS. 4-10D illustrate exemplary embodiments of processes by which a chip 304 is assembled onto a contact lens substrate 418 in accordance with aspects described herein. FIG. 4 illustrates a high level overview of processes by which a chip 304 is assembled onto a contact lens substrate 418 while FIGS. 5A-10D illustrate detailed steps in various processes by which a chip 304 is assembled onto a contact lens substrate 418. After one or more chips have been assembled onto contact lens substrate 418, the contact lens substrate can be modified into a contact lens. In particular, the contact lens substrate 418 can be molded into the shape of a contact lens to become the contact lens substrate layer (e.g. layer 214) in an assembled contact lens (e.g. lenses 200, 202, 204 and the like). In various aspects, the contact lens substrate 418 can include one or more of the structure and/or functionality of contact lens substrate layer 214 (and vice versa). In particular, it should be appreciated that contact lens substrate 418 can comprise the materials described with reference to contact lens substrate layer 214.

Turning initially to FIG. 4, a silicon chip 304 that has been sized to a suitable size for integration into a contact lens (e.g. having a thickness less than 100 microns and sides less than about 1 mm) is depicted having metal lines 402 provided thereon. In particular, after a silicon chip 304 is created via process 300, prior to integration onto a contact lens substrate 418, the silicon chip 304 can be processed to form various functional features of the silicon chip, including at least chip contact pads. Chip contact pads provide the contact point for electrically connecting a chip 304 to substrate 418 and/or other electrical component. In an aspect, traditional metal chip contact pads (not depicted) can be created on a surface of chip 304. For example, metal chip pads in the form of small and thin sheets of metal in the shape of squares or rectangles can be formed on a surface of the chip 304 to create the chip contact pads. Such metal contact pads can have sides less than 100 microns.

However, in another aspect, as depicted in FIG. 4, metals lines 402 are patterned onto a surface of chip 304. For example, metal lines 402 can be patterned onto a surface 406 of a chip 304 using photolithography. These metal lines 402 serve as chip contact pads for the chip 304 and also serve as wires to connect the chip 304 to other chips and/or components of a contact lens (e.g. antennas, sensors, LEDs, and etc.) in which the chip 304 is integrated. For example, intersection points 404 of metal lines 402 can serve as the chip contact pads of chip 304. However, it should be appreciated that any point of a metal line 402 can serve as a chip contact pad. In addition, although intersecting parallel metal lines 402 are shown forming a grid pattern on chip 304, such a line configuration is merely depicted for exemplary purposes. In particular, lines 402 can be formed in any pattern, in includes patterns having non-intersecting lines and patterns having non-parallel lines.

In an aspect, the surface of chip 304 on which the metal lines are formed, surface 406, is a substantially flat polymer layer provided on the chip 304. According to this aspect, the metal lines 402 are patterned onto the substantially flat polymer layer using photolithography. For example, the polymer layer can include but is not limited to parylene, polyimide, and polyethylene terephthalate (PET).

Contact lens substrate 418 is also presented having lens contact pads located on a surface thereof. In an aspect, lens contact pads provide the contact points for electrically and/or physically connecting the substrate 418 with the chip 304 and/or electrically connecting other electrical components provided within a contact lens in which the lens substrate 418 is integrated, to the chip 304. In an aspect, traditional metal chip contact pads 414 can be created on a surface of lens substrate 418. For example, metal chip pads in the form of small and thin sheets of metal in the shape of squares or rectangles can be formed on a surface of the lens substrate 418 to create the lens contact pads. Such metal contact pads can have sides less than 100 microns.

However, in another aspect, metals lines 416 are patterned onto a surface of contact lens substrate 418 in a same or similar fashion as metal lines 402 patterned on chip 304. For example, metal lines 416 can be patterned onto a surface of lens substrate 418 using photolithography. As with metal lines 402, metal lines 416 can serve as lens contact pads for the lens substrate 418 and also serve as wires to connect the chip 304 to other chips and/or components of a contact lens (e.g. antennas, sensors, LEDs, and etc.) in which the chip 304 is integrated. In addition, although intersecting parallel metal lines 416 are shown forming a grid pattern on substrate 418 such a line configuration is merely depicted for exemplary purposes. In particular, lines 416 can be formed in any pattern, in includes patterns having non-intersecting lines and patterns having non-parallel lines.

In an aspect, the lens substrate and/or a surface of lens substrate 418 on which the metal lines 416 are formed is a substantially flat polymer layer. According to this aspect, the metal lines 416 are patterned onto the substantially flat polymer layer using photolithography. For example, the polymer layer can include but is not limited to parylene, polyimide, and polyethylene terephthalate (PET).

It should be appreciated that both traditional metal contact pads 414 and metal line contact pads 416 are provided on lens substrate 418 merely for exemplary purposes. Further, although only a partial area of the lens substrate 418 is presented having contact pads thereon, it should be appreciated that any portion of the substrate 418 can be provided with contact pads. For example, the entire surface of the substrate 418 can be patterned with metal lines or square metal pads. According to this example, a subset of the metal lines/metal pads can be selectively employed as the contact pads for assembly of a chip thereon. In other words, a subset of the metal lines/metal pads can be selectively employed as an assembly site for assembly of a chip thereon and the substrate can be provided with a plurality of potential assembly sites. As used herein, the term assembly site refers to an area of substrate 418 having lens contact pads that can be aligned with the contact pads of a chip.

In order to attach silicon chip 304 to contact lens substrate 418, an assembly bonding material (not shown) is applied to either the chip or the lens substrate 418. In an aspect, the assembly bonding material includes an anisotropic conductive film (ACF) or an anisotropic conductive paste (ACP). ACF and ACP are materials that establish a conducting path when pressed between two metal pads, such as a lens contact pad and a chip contact pad. According to this aspect, an ACF or ACP is applied over an entire assembly site on the substrate 418 (and/or the chip) having lens (or chip) contact pads therein so as to cover the contact pads and the area between and around the contact pads. With this aspect, assembly bonding material does not need to be applied to the contact pads individually.

After application of the ACF or ACP, the silicon chip 304 is then flipped over, following arrow 408, so that the surface 406 of the silicon chip 304 having the chip contact pads (e.g. the surface having the metal lines 402) faces a surface of the contact lens substrate 418 having the lens contact pads thereon. Dashed lines 402 presented on flipped chip 304 are indicative of the metal lines 402 now on the underside 306 of the chip. The chip 304 is then lowered onto the substrate 418 and the chip contact pads are aligned with the lens contact pads. The chip 304 is then assembled onto the lens substrate via pressing the chip 304 onto the ACF or ACP and heating the chip 304/substrate 418 assembly to cure or solidify the chip 304 connection with the substrate 418. In particular, the ACP or ACF is activated in order to secure chip 304 to substrate 418 in part by the heating. For example, activation of an ACP or ACF can include boiling a flux out of the ACP or ACF to create a conductive path between the chip contact pads and lens contact pads and to create an adhesive (e.g. an underfill) material that bonds chip 304 to substrate 418. In an aspect, heating of the of the chip 304/substrate 418 assembly is performed so that conduction results in a single direction so that the contact pads do not short.

In another aspect, the assembly bonding material includes a solder solution or solder paste. According to this aspect, solder solution or solder paste (not shown) is applied to either the chip contact pads or the lens contact pads in a particular assembly site. In an aspect, the solder solution/paste is applied to respective ones of either the chip contact pads or the lens contact pads using a syringe. The silicon chip 304 is then flipped over, following arrow 408, so that the surface 406 of the silicon chip 304 having the chip contact pads (e.g. the surface having the metal lines 402) faces a surface of the contact lens substrate 418 having the lens contact pads thereon. Dashed lines 402 presented on flipped chip 304 are indicative of the metal lines 402 now on the underside 306 of the chip. The chip 304 is then lowered onto the substrate 418 and the chip contact pads are aligned with the lens contact pads. Head and pressure are then applied to at least one of the chip 304 or the lens substrate 418 so that the solder solution is flowed and solidified so as to bond the chip 304 to the lens substrate 418. Arrow 410 shows an example where the chip 304 is bonded to an assembly site on the substrate 418 that comprises metal squares as contact pads. Arrow 412 shows an example where the chip 304 is bonded to an assembly site on the substrate 418 that comprises metal lines as contact pads.

In some aspects, an underfill is applied to the lens substrate/chip complex in order to hold the chip 304 onto the substrate 418. In particular, connections established between the chip 304 and the substrate 418 can be relatively weak when using a solder solution/paste as the assembly bonding material. Accordingly, an underfill material can be applied between the chip 304 and the substrate so as to flow around the respective solder pads and solidified solder material to further facilitate bonding of the chip 304 to the substrate. The underfill can include a non-conductive or substantially non-conductive material such as an epoxy or adhesive.

In an aspect, flipping 408, alignment of chip 304 with contact pads on lens substrate 418, and bonding is performed using a flip chip bonder. As used herein, the term flip chip bonder refers to a tool that performs functions and features of traditional flip chip bonding methods, including at least flipping of chip 304, alignment of chip 304 with substrate 418, and application of heat and pressure to chip 304 and substrate 418 such that the chip 304 and the substrate 418 bond via the solder solution provided there between.

In an aspect, the assembly bonding material that is applied to the lens substrate or chip is a low activation temperature material. For example, in some aspects, the assembly bonding material includes an ACF or an ACP that has a low activation temperature, such as below 200° C. In other aspects, the assembly bonding material includes a solder material that has a low melting point, such as below 200° C. In another aspect, the assembly bonding material can have an activation temperature or boiling point less than 150° C. In another aspect, the assembly bonding material can have an activation temperature or boiling point less than 100° C. In yet another aspect, the assembly bonding material can have an activation temperature or boiling point less than 85° C. Still in yet another aspect, the assembly bonding material can have an activation temperature or boiling point less than 65° C.

Some exemplary low temperature solder solutions/pastes that can be employed as the assembly bonding material can include but are not limited to solutions or pastes having varying ratios of indium, tin, and/or bismuth. For example, indium alloy number 19 from Indium Corp. can be employed as an exemplary solder solution and has a ration of 51% In, 32.5% Bi, and 16.5 Sn with a melting temperature of about 60° C. In an aspect, an employed solder solution/paste is lead-free so as not to disrupt an eye in which a contact lens, having a chip 304 integrated therein, is worn. In some aspects, the solder solution can also be mixed with a flux or acidic solution (such as HCL and water) to prevent or reduce oxidation of the solder solution. Some exemplary fluxes can include but are not limited to TACFlux® 020B and Indalloy Flux #4-OA from Indium Corp. Additionally, a commercially available solder solution can be employed as the assembly bonding material that is formed as a paste suspended in a solder solution, such NC-SMQ®90 Solder Paste from Indium Corp.

Looking now to FIGS. 5A-5E, illustrated is an exemplary process 500 by which a silicon chip is assembled onto a contact lens substrate 418 in accordance with aspects described herein. In FIGS. 5A-5E, it should be appreciated that only a portion of contact lens substrate 418 is presented for exemplary purposes. Process 500 follows in part, arrow 410 of FIG. 4. In particular, process 500 present an embodiment where chip 304 is bonded to an assembly site on the substrate 418 that comprises metal squares 414 as contact pads.

Figure 5A:
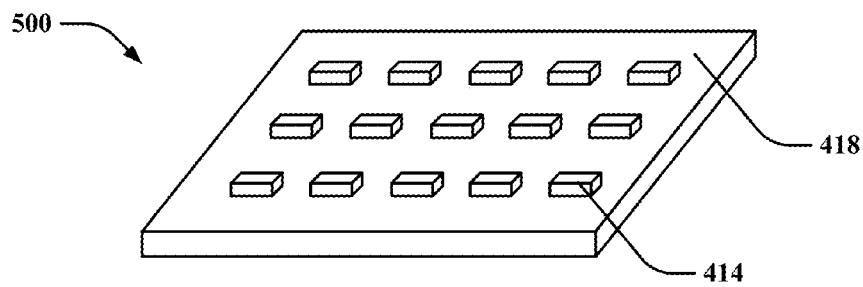
FIGS. 5A-5E illustrate an exemplary process 500 by which a silicon chip is assembled onto a contact lens substrate in accordance with aspects described herein.

As seen in FIG. 5A, a contact lens substrate 418 is provided having a plurality of metal square contact pads 414 created thereon. A chip 304 is assembled to substrate 418 using either solder solution according to FIG. 5B or a solder film or paste including ACF or ACP respectively according to FIG. 5C. Accordingly, process 500 can proceed with steps according to FIG. 5B or according to FIG. 5C.

Figure 5B:
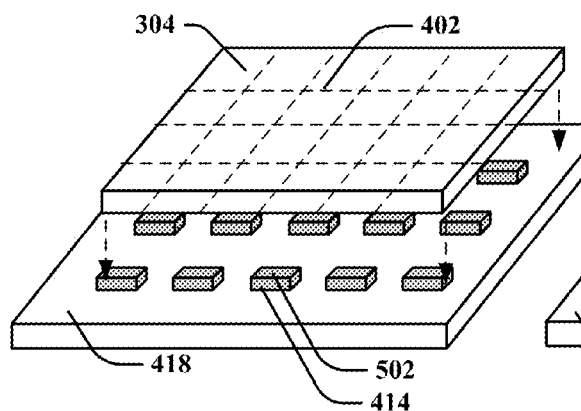

In FIG. 5B, solder solution 502 is applied to each of the lens contact pads 414. (The solder solution 502 is represented by the darkening of the lens contact pads 414 as compared to the lens contact pads 414 of FIG. 5A). In an aspect, the solder solution 502 is selectively applied to each of the lens contact pads 414 using a syringe, pipette, needle, or other precise applicator tool. Then a chip 304 having chip contact pads in the form of metal lines 402 is flipped over and aligned with lens substrate 418. In particular, the chip contact pads, (such as the intersection points of the metal lines 402), are aligned with each of the lens contact pads 414 having solder solution 502 thereon.

Figure 5C:
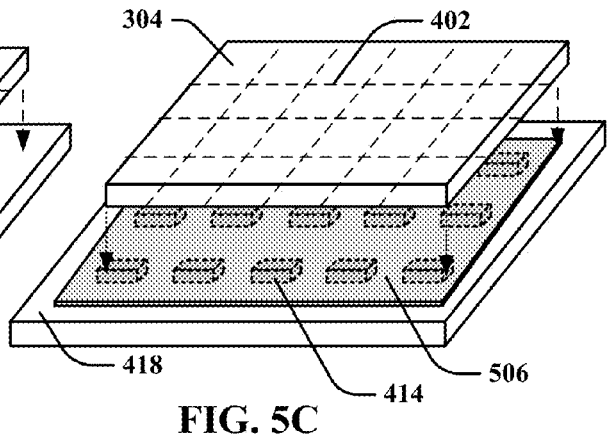

In FIG. 5C, (the alternative to FIG. 5B), an ACF or ACP 506 is applied to the lens substrate 418 so as to cover the lens contact pads 414 and the area around the respective lens contact pads 414 in the assembly site. Then a chip 304 having chip contact pads in the form of metal lines 402 is flipped over and aligned with lens substrate 418. In particular, the chip contact pads, (such as the intersection points of the metal lines 402), are aligned with each of the lens contact pads 414 having an ACF or ACP thereon.

Figure 5D:
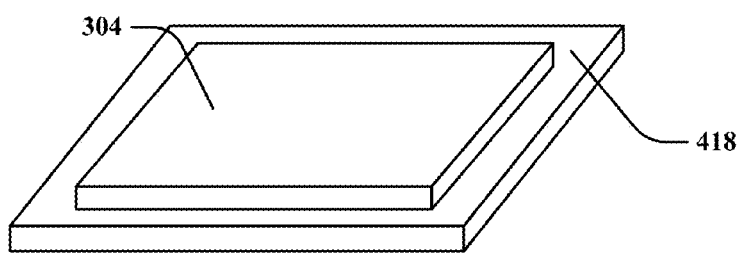
Figure 5E:
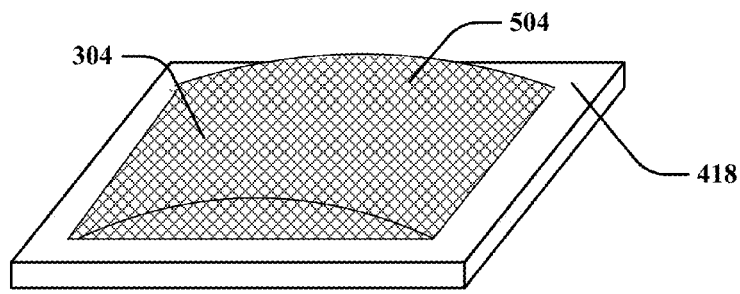

In FIG. 5D, the chip 304 is lowered onto the lens substrate 418 and the chip is bonded to the lens substrate via the solder solution or the ACF/ACP in response to the application of pressure and/or heat. For example, a flip chip bonder can perform the flipping, aligning and bonding aspects of method 500. In an aspect, heat is applied at a temperature less than 200° C. to substantially only the area of the substrate 418 where the chip 304 is being assembled (e.g. the assembly sites) so as to cause no or limited damage to the remaining area of the substrate. In FIG. 5E, once the solder solution or ACF/ACP has been solidified, hardened and/or cured, in an aspect, the chip 304 can be sealed onto the lens substrate 418 using a sealant 504. The sealant 504 can cover and/or otherwise coat the chip 304 to hold the chip 304 in place on the lens substrate 418 and/or to make the lens substrate/chip complex biocompatible. In an aspect, (not shown), the entire substrate/chip complex can be coated in a sealant 504. For example, the entire substrate/chip complex can be dipped or rinsed with a sealant 504. In an aspect, the sealant 504 is parylene or polyimide.

FIGS. 6A-6D, illustrate an alternative perspective of exemplary process 500 by which a silicon chip is assembled onto a contact lens substrate 418 in accordance with aspects described herein. In particular, FIGS. 6A-6D present cross-sectional views of chip 304 and lens 418 during process 500.

Figure 6A:
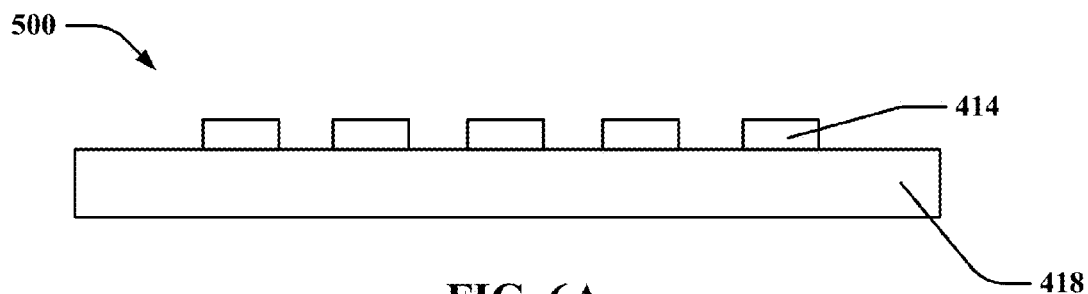
FIGS. 6A-6D illustrate another an alternative perspective of exemplary process 500 by which a silicon chip is assembled onto a contact lens substrate in accordance with aspects described herein.
Figure 6B:
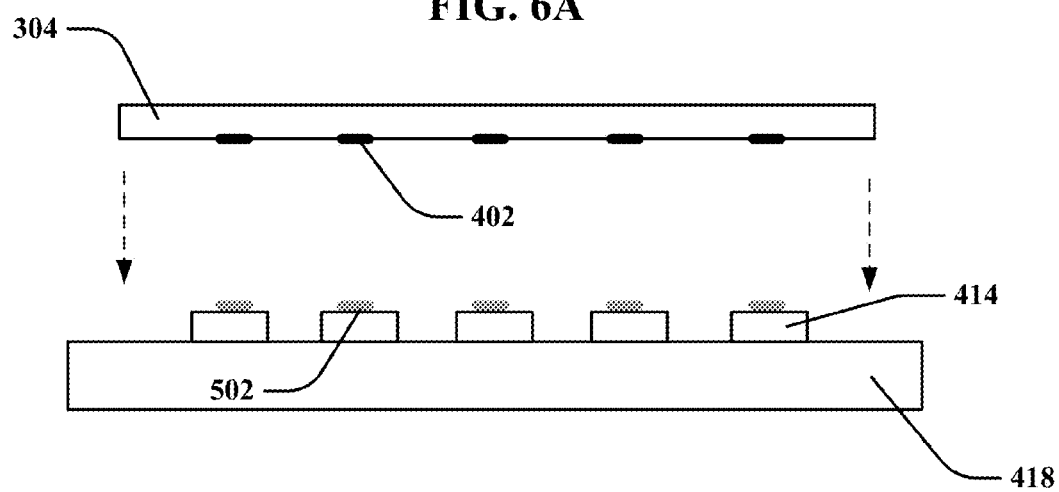

As seen in FIG. 6A, a contact lens substrate 418 is provided having a plurality of metal square contact pads 414 created thereon. In FIG. 5B, solder solution 502 is applied to each of the lens contact pads 414. In an aspect, the solder solution 502 is selectively applied to each of the lens contact pads 414 using a syringe, pipette, needle, or other precise applicator tool. Then a chip 304 having chip contact pads 402 is aligned with lens substrate 418. In particular, the chip contact pads 402 are aligned with each of the lens contact pads 414 having solder solution 502 thereon. In an aspect, the chip contact pads 402 are the intersection points 404 of the metal lines 402 as presented on chip 304 in FIG. 4.

Figure 6C:
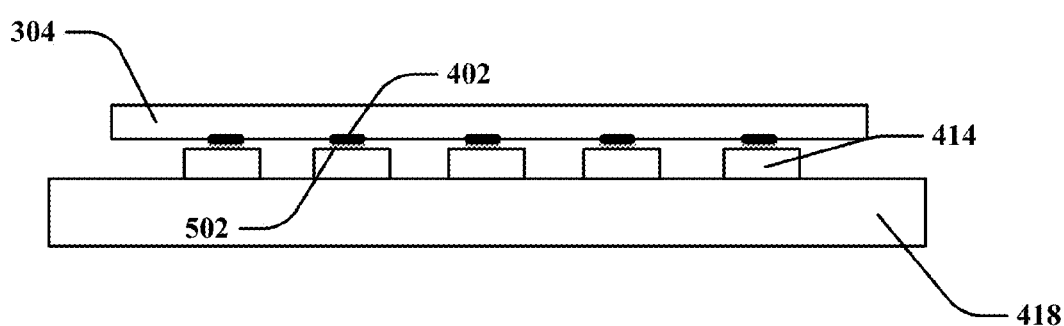
Figure 6D:
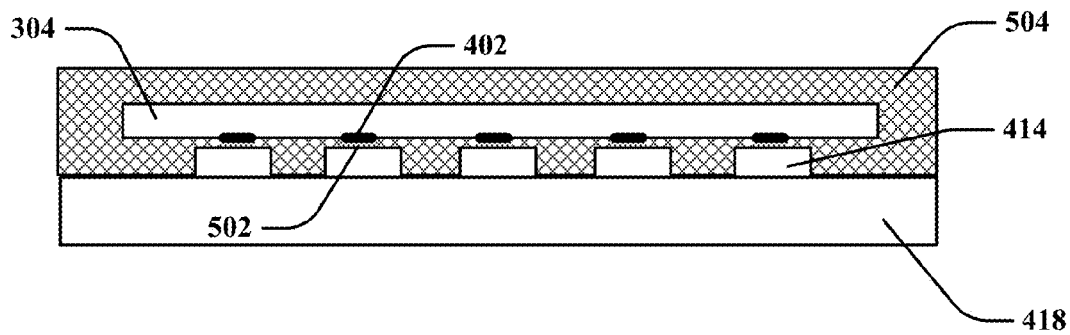

In FIG. 6C, the chip 304 is lowered onto the lens substrate 418 and the chip is bonded to the lens substrate via the solder solution in response to the application of pressure and/or heat. In an aspect, heat is applied at a temperature less than 200° C. to substantially only the area of the substrate 418 where the chip 304 is being assembled (e.g. the assembly sites) so as to cause limited damage to the remaining area of the substrate. For example, a flip chip bonder can perform the flipping, aligning and bonding aspects of method 500. In an aspect, an underfill material (not shown) can be applied between the lens substrate 418 and the chip 304 so as to fill in gaps between the solidified solder material and further adhere the chip 304 to the substrate 418. In FIG. 6D, once the solder solution has been solidified, hardened and/or cured, in an aspect, the chip 304 can be sealed onto the lens substrate 418 using a sealant 504. The sealant 504 can cover and/or otherwise coat the chip 304 to hold the chip 304 in place on the lens substrate 418 and/or to make the lens substrate/chip complex biocompatible. In an aspect, (not shown), the entire substrate/chip complex can be coated in a sealant 504. For example, the entire substrate/chip complex can be dipped or rinsed with a sealant 504.

Looking now to FIGS. 7A-7D, illustrated is another exemplary process 700 by which a silicon chip is assembled onto a contact lens substrate 418 in accordance with aspects described herein. In FIGS. 7A-7D, it should be appreciated that only a portion of contact lens substrate 418 is presented for exemplary purposes. Process 700 follows in part, arrow 412 of FIG. 4. In particular, process 700 present an embodiment where chip 304 is bonded to an assembly site on the substrate 418 that comprises metal lines 416 as contact pads.

Figure 7A:
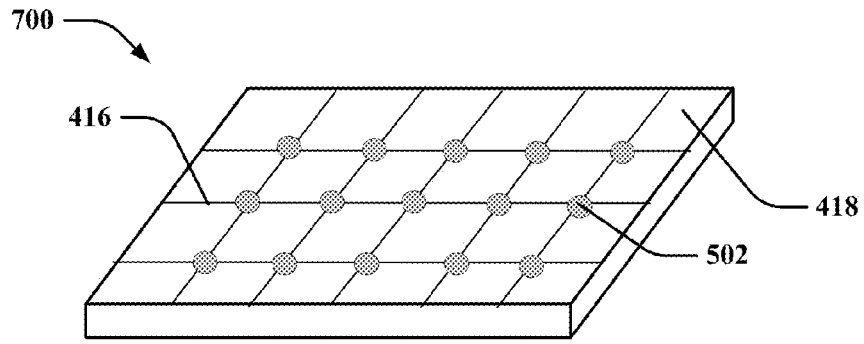
FIGS. 7A-7D illustrate another exemplary process 700 by which a silicon chip is assembled onto a contact lens substrate in accordance with aspects described herein.
Figure 7B:
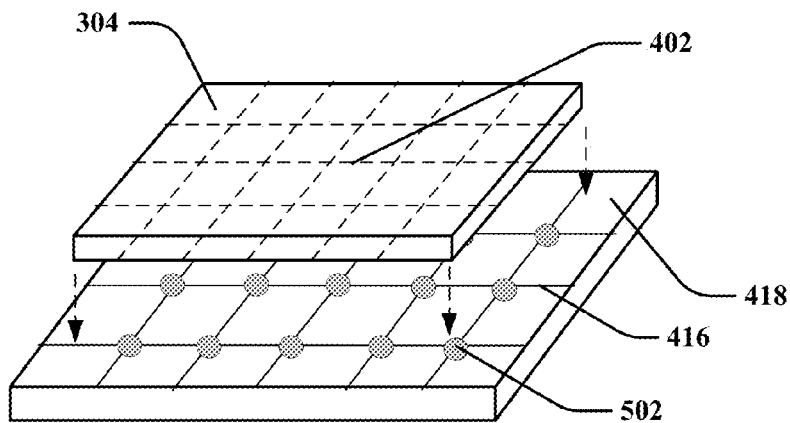

As seen in FIG. 7A, a contact lens substrate 418 is provided having a plurality of metal lines 416 created thereon. The metal lines 416 serve as the lens contact pads. In an aspect, the intersection point of the metal lines in particular serve as the lens contact pads. According to this aspect, solder solution 502 is applied to the lens contact pads 416 at each metal line intersection point. In an aspect, the solder solution 502 is selectively applied to each of the lens contact pads 416 using a syringe, pipette, needle, or other precise applicator tool. In FIG. 7B, a chip 304 having chip contact pads in the form of metal lines 402 is flipped over and aligned with lens substrate 418. In particular, the chip contact pads, (such as the intersection points of the metal lines 402), are aligned with each of the lens contact pads 416, the metal line 416 intersection points, having solder solution 502 thereon.

Figure 7C:
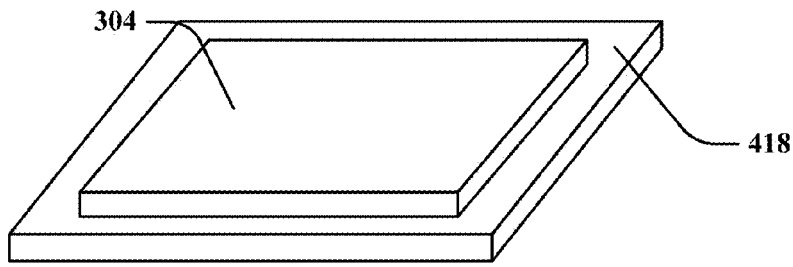
Figure 7D:
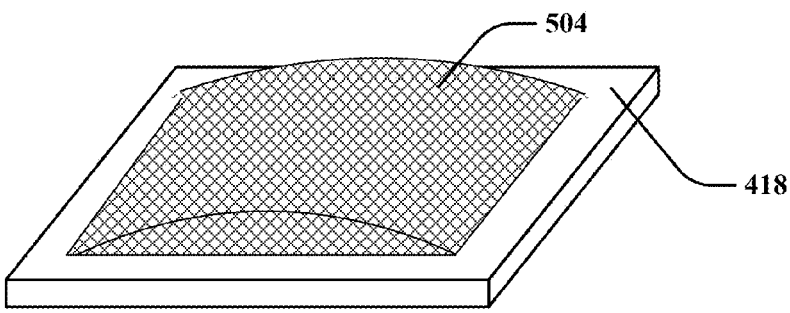

In FIG. 7C, the chip 304 is lowered onto the lens substrate 418 and the chip is bonded to the lens substrate via the solder solution in response to the application of pressure and/or heat. In an aspect, heat is applied at a temperature less than 200° C. to substantially only the area of the substrate 418 where the chip 304 is being assembled (e.g. the assembly sites) so as to cause no or limited damage to the remaining area of the substrate. For example, a flip chip bonder can perform the flipping, aligning and bonding aspects of method 700. In an aspect, an underfill material (not shown) can be applied between the lens substrate 418 and the chip 304 so as to fill in gaps between the solidified solder material and further adhere the chip 304 to the substrate 418. In FIG. 7D, once the solder solution has been solidified, hardened and/or cured, in an aspect, the chip 304 can be sealed onto the lens substrate 418 using a sealant 504. The sealant 504 can cover and/or otherwise coat the chip 304 to hold the chip 304 in place on the lens substrate 418 and/or to make the lens substrate/chip complex biocompatible. In an aspect, (not shown), the entire substrate/chip complex can be coated in a sealant 504. For example, the entire substrate/chip complex can be dipped or rinsed with a sealant 504.

FIGS. 8A-8D, illustrate an alternative perspective of exemplary process 700 by which a silicon chip is assembled onto a contact lens substrate 418 in accordance with aspects described herein. In particular, FIGS. 8A-8D present cross-sectional views of chip 304 and lens 418 during process 700.

Figure 8A:
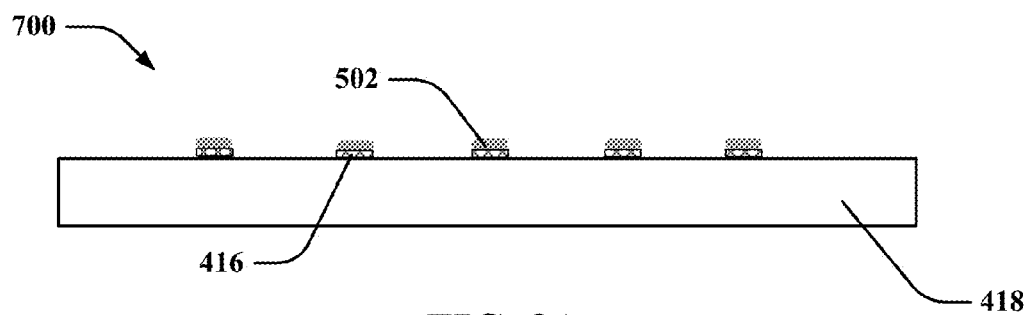
FIGS. 8A-8D illustrate another an alternative perspective of exemplary process 800 by which a silicon chip is assembled onto a contact lens substrate in accordance with aspects described herein.
Figure 8B:
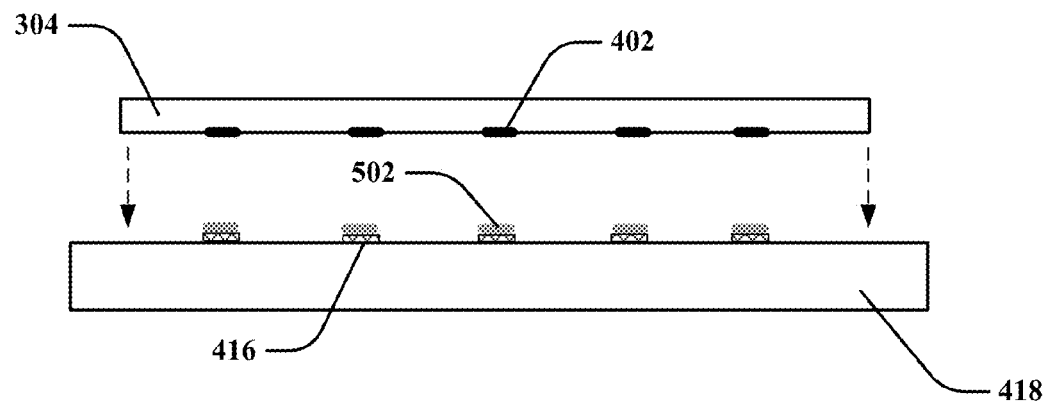

As seen in FIG. 8A, a contact lens substrate 418 is provided having a plurality of contact pads 416 created thereon. The contact pads 416 are formed from metal lines such as metal lines 416 that have been patterned onto the lens substrate 418 via photolithography. In an aspect, the contact pads 416 include intersection points of metal lines 416 as depicted in FIG. 4. The contact pads 416 further have solder solution 502 applied thereto. In an aspect, the solder solution 502 is selectively applied to each of the lens contact pads 416 using a syringe, pipette, needle, or other precise applicator tool. In FIG. 8A, a chip 304 having chip contact pads 402 is aligned with lens substrate 418. In particular, the chip contact pads 402 are aligned with each of the lens contact pads 416 having solder solution 502 thereon. In an aspect, the chip contact pads 402 are similarly intersection points 404 of the metal pads 402 as presented on chip 304 in FIG. 4.

Figure 8C:
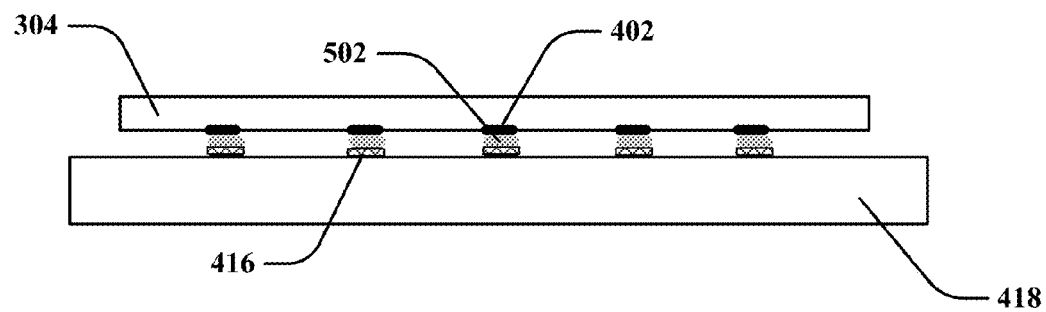
Figure 8D:
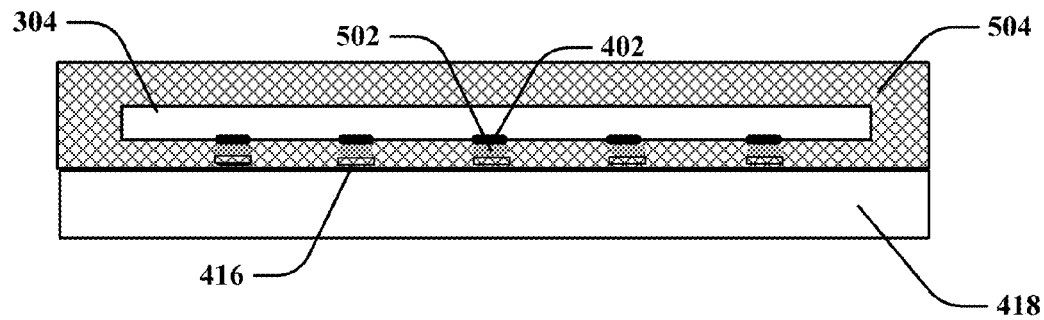

In FIG. 8C, the chip 304 is lowered onto the lens substrate 418 and the chip is bonded to the lens substrate via the solder solution in response to the application of pressure and/or heat. In an aspect, heat is applied at a temperature less than 200° C. to substantially only the area of the substrate 418 where the chip 304 is being assembled (e.g. the assembly sites) so as to cause no or limited damage to the remaining area of the substrate. For example, a flip chip bonder can perform the flipping, aligning and bonding aspects of method 700. In an aspect, an underfill material (not shown) can be applied between the lens substrate 418 and the chip 304 so as to fill in gaps between the solidified solder material and further adhere the chip 304 to the substrate 418. In FIG. 8D, once the solder solution has been solidified, hardened and/or cured, in an aspect, the chip 304 can be sealed onto the lens substrate 418 using a sealant 504. The sealant 504 can cover and/or otherwise coat the chip 304 to hold the chip 304 in place on the lens substrate 418 and/or to make the lens substrate/chip complex biocompatible. In an aspect, (not shown), the entire substrate/chip complex can be coated in a sealant 504. For example, the entire substrate/chip complex can be dipped or rinsed with a sealant 504.

Figure 9A:
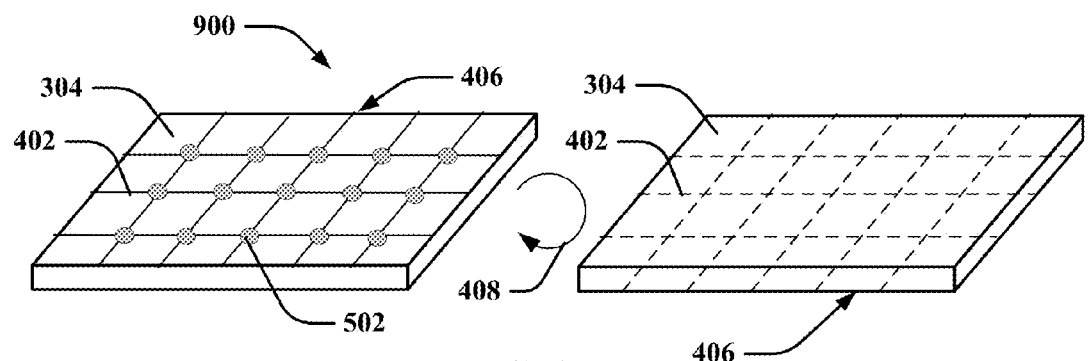
FIGS. 9A-9D illustrate another exemplary process 900 by which a silicon chip is assembled onto a contact lens substrate in accordance with aspects described herein.
Figure 9B:
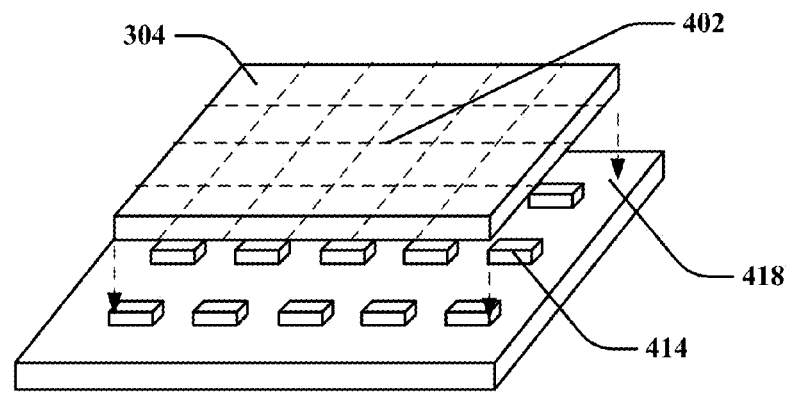

Looking now to FIGS. 9A-9D, illustrated is another exemplary process 900 by which a silicon chip is assembled onto a contact lens substrate 418 in accordance with aspects described herein. In FIGS. 9A-9B, it should be appreciated that only a portion of contact lens substrate 418 is presented for exemplary purposes. Process 900 presents an embodiment where chip 304 is bonded to an assembly site on the substrate 418 that comprises metal square 414 as contact pads and where the bonding solution is applied to the chip contact pads.

As seen in FIG. 9A, a silicon chip 304 is provided having a plurality of metal lines 402 created thereon. The metal lines 402 serve as the chip contact pads. In an aspect, the intersection points of the metal lines in particular serve as the chip contact pads. According to this aspect, solder solution 502 is applied to the chip contact pads 402 at each metal line intersection point. In an aspect, the solder solution 502 is selectively applied to each of the chip contact pads 402 using a syringe, pipette, needle, or other precise applicator tool. The chip is 304 is further flipped over following arrow 408 so that the chip contact pads having the solder solution applied thereto can face a surface of the lens substrate 418 having contact pads 414 thereon. The dashed lines on flipped chip 304 are indicative of the chip contact pads now on the underside 406 of the chip.

In FIG. 9B, the flipped chip 304 having the chip contact pads with solder applied is aligned with lens substrate 418. In particular, the chip contact pads, (such as the intersection points of the metal lines 402), are aligned with each of the lens contact pads 414. Lens substrate 418 is provided having contact pads 414 located thereon. Although lens contact pads 414 are presented as metal squares, it should be appreciated that the lens contact pads can be in the form of metal lines.

Figure 9C:
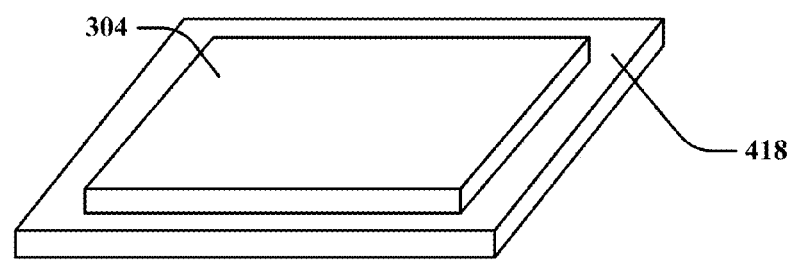
Figure 9D:
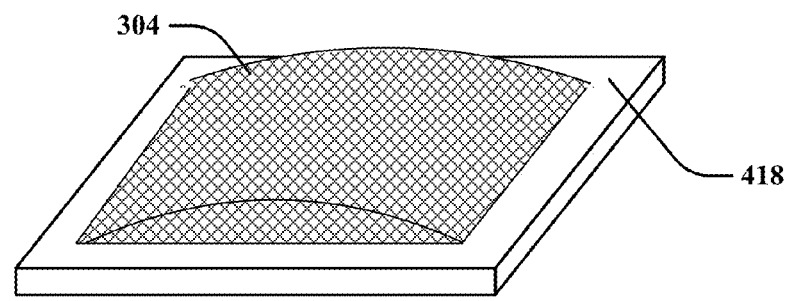

In FIG. 9C, the chip 304 is lowered onto the lens substrate 418 and the chip is bonded to the lens substrate via the solder solution in response to the application of pressure and/or heat. In an aspect, heat is applied at a temperature less than 200° C. to substantially only the area of the substrate 418 where the chip 304 is being assembled (e.g. the assembly sites) so as to cause no or limited damage to the remaining area of the substrate. For example, a flip chip bonder can perform the flipping, aligning and bonding aspects of method 900. In an aspect, an underfill material (not shown) can be applied between the lens substrate 418 and the chip 304 so as to fill in gaps between the solidified solder material and further adhere the chip 304 to the substrate 418. In FIG. 9D, once the solder solution has been solidified, hardened and/or cured, in an aspect, the chip 304 can be sealed onto the lens substrate 418 using a sealant 504. The sealant 504 can cover and/or otherwise coat the chip 304 to hold the chip 304 in place on the lens substrate 418 and/or to make the lens substrate/chip complex biocompatible. In an aspect, (not shown), the entire substrate/chip complex can be coated in a sealant 504. For example, the entire substrate/chip complex can be dipped or rinsed with a sealant 504.

FIGS. 10A-10D, illustrate an alternative perspective of exemplary process 900 by which a silicon chip is assembled onto a contact lens substrate 418 in accordance with aspects described herein. In particular, FIGS. 10A-10D present cross-sectional views of chip 304 and lens 418 during process 900.

Figure 10A:
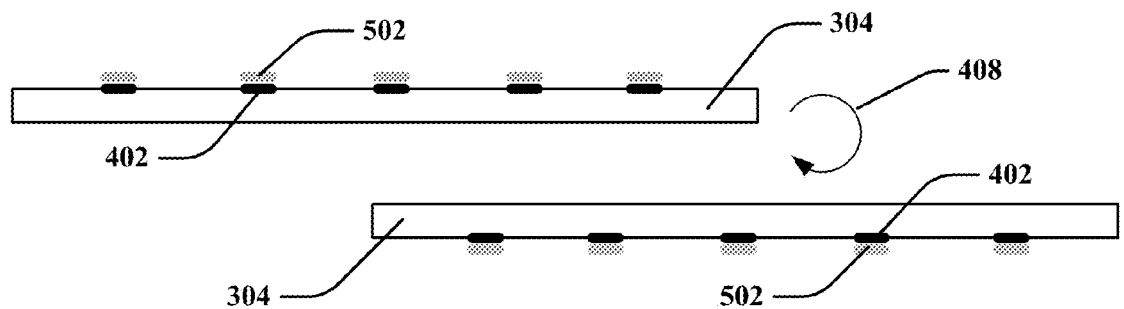
FIGS. 10A-10D illustrate another an alternative perspective of exemplary process 900 by which a silicon chip is assembled onto a contact lens substrate in accordance with aspects described herein.

As seen in FIG. 10A, a silicon chip 304 is provided having a plurality of metal lines 402 created thereon. The metal lines 402 serve as the chip contact pads. In an aspect, the contact pads 402 are the intersection points of the metal lines 402 (point 404) as presented in FIG. 4. According to this aspect, solder solution 502 is applied to the chip contact pads 402 at each metal line intersection point. In an aspect, the solder solution 502 is selectively applied to each of the chip contact pads 402 using a syringe, pipette, needle, or other precise applicator tool. The chip is 304 is further flipped over following arrow 408 so that the chip contact pads having the solder solution applied thereto can face a surface of the lens substrate 418 having contact pads 414 thereon.

Figure 10B:
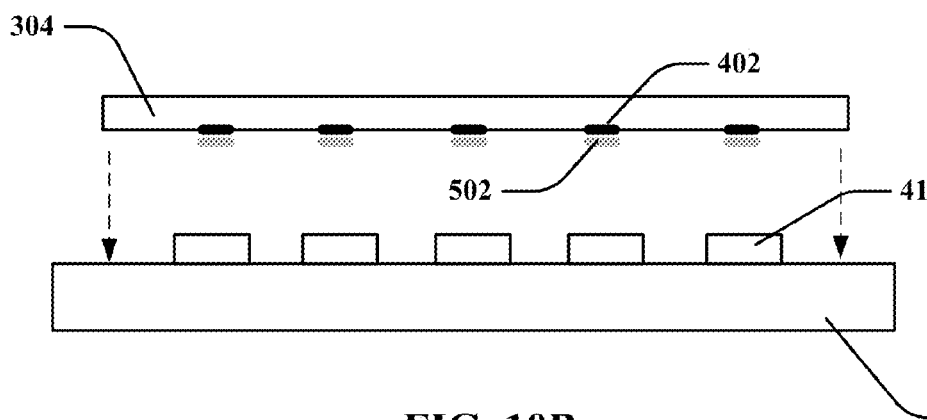

In FIG. 10B, the flipped chip 304 having the chip contact pads with solder applied is aligned with lens substrate 418. In particular, the chip contact pads, (such as the intersection points of the metal lines 402), are aligned with each of the lens contact pads 414. Lens substrate 418 is provided having contact pads 414 located thereon. Although lens contact pads 414 are presented as metal squares, it should be appreciated that the lens contact pads can be in the form of metal lines.

Figure 10C:
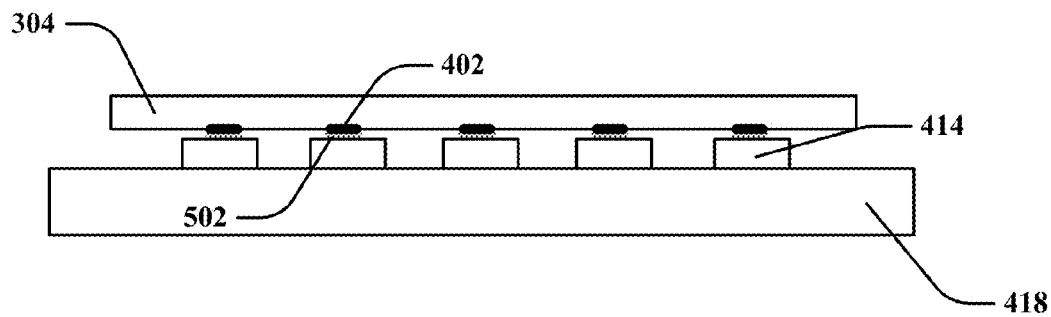
Figure 10D:
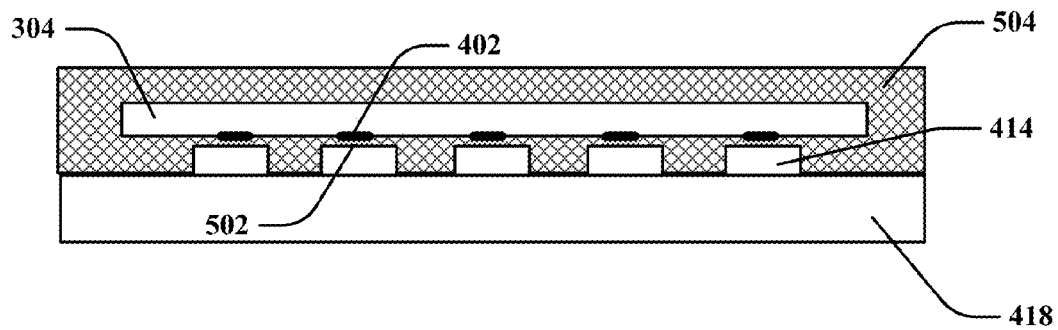

In FIG. 10C, the chip 304 is lowered onto the lens substrate 418 and the chip is bonded to the lens substrate via the solder solution in response to the application of pressure and/or heat. In an aspect, heat is applied at a temperature less than 200° C. to substantially only the area of the substrate 418 where the chip 304 is being assembled (e.g. the assembly sites) so as to cause no or limited damage to the remaining area of the substrate. For example, a flip chip bonder can perform the flipping, aligning and bonding aspects of method 900. In an aspect, an underfill material (not shown) can be applied between the lens substrate 418 and the chip 304 so as to fill in gaps between the solidified solder material and further adhere the chip 304 to the substrate 418. In FIG. 10D, once the solder solution has been solidified, hardened and/or cured, in an aspect, the chip 304 can be sealed onto the lens substrate 418 using a sealant 504. The sealant 504 can cover and/or otherwise coat the chip 304 to hold the chip 304 in place on the lens substrate 418 and/or to make the lens substrate/chip complex biocompatible. In an aspect, (not shown), the entire substrate/chip complex can be coated in a sealant 504. For example, the entire substrate/chip complex can be dipped or rinsed with a sealant 504.

Figure 11A:
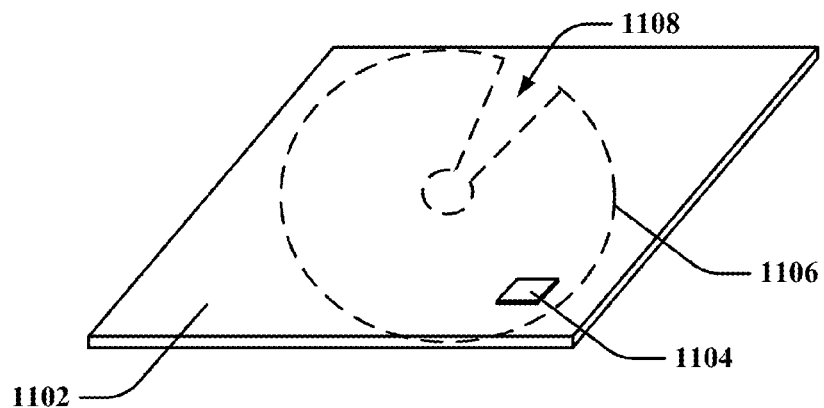
FIGS. 11A-11C illustrate a process for employing a contact lens substrate having a silicon chip bonded thereon to form a contact lens in accordance with aspects described herein.
Figure 11B:
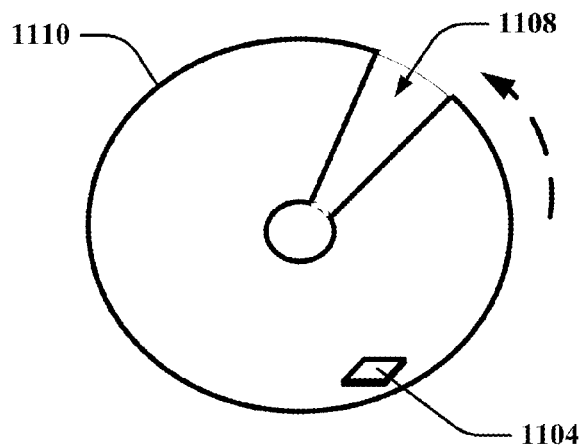
Figure 11C:
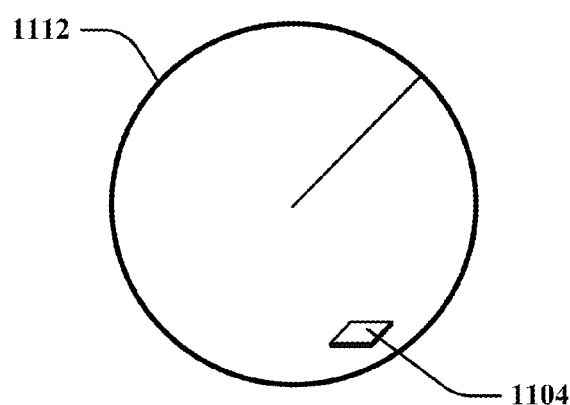

Referring now to FIGS. 11A-11C, illustrated is a process for employing a contact lens substrate having a silicon chip bonded thereon to form a contact lens in accordance with aspects described herein. As seen in FIG. 11A, a contact lens substrate 1102 having a silicon chip 1104 bonded thereon is provided. In various aspects, the contact lens substrate 1102 and chip 1104 can include one or more of the structure and/or functionality of contact lens substrate layer 214 and chip 206, and/or the contact lens substrate 418 and chip 304 (and vice versa). In an aspect, the chip 1104 is sealed to the contact lens substrate 1102 via a sealant (e.g. parylene).

The contact lens substrate 1102 is used to form a contact lens form 1112. In an aspect, the contact lens substrate 1102 is molded into a shape of a contact lens form 1112. (e.g. a round and curved shape). In particular, the contact lens substrate 1102 is molded to match the curvature of an eye in which the contact lens is to be worn. In some aspects, in order to facilitate molding the contact lens substrate 1102, the contact lens substrate 1102 is cut into a shape that can be formed into the shape of a contact lens. For example, as seen in FIG. 11B, the contact lens substrate 1102 can be cut into a circular shape or ring shape 1110. The cut substrate 1110 shown in FIG. 11B is cut out of the contact lens substrate 1102 along dotted line pattern 1106. The cut substrate 1110 can include cut slits or incisions 1108 on inner and/or outer edges of the ring to facilitate forming the cut substrate 1110 into a contact lens shape. The cut substrate 1110 is cut out of the contact lens substrate 1102 so as to include the attached chip 1104.

FIG. 11C shows a two-dimensional view of a contact lens form 1112 formed out of contact lens substrate 1102. Contact lens form 1112 includes chip 1104. In an aspect, contact lens form 1112 is formed by closing off the incisions 1108 of cut substrate 1110. For example, the open edges of cut substrate 1110 can be bended and brought together (e.g. following the dashed arrow of FIG. 11B) to form the contact lens form 1112 of FIG. 11C.

Figure 12A:
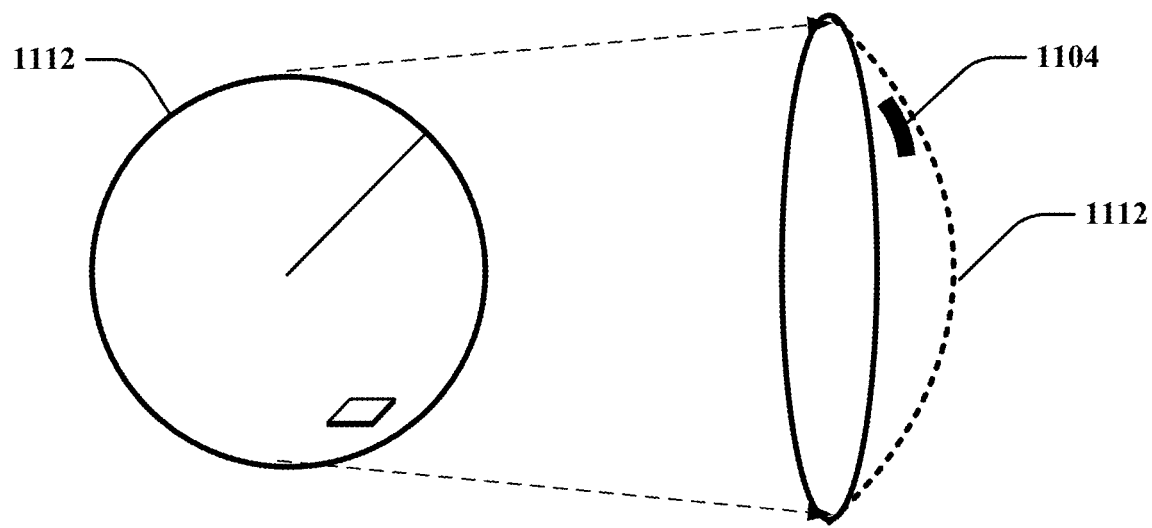
FIG. 12A presents an alternative, three-dimensional view of a contact lens form in accordance with aspects described herein.

FIG. 12A presents an alternative, three-dimensional view of contact lens form 1112. In an aspect, contact lens form 1112 can be employed as a finished, wearable/functional contact lens. Contact lens form matches the shape of a contact lens and forms to the curvature of the eye in which it is to be worn. Contact lens form further includes the chip 1104 integrated thereon. However, in another aspect, contact lens form is further processed to form a finished, wearable/functional contact lens.

Figure 12B:
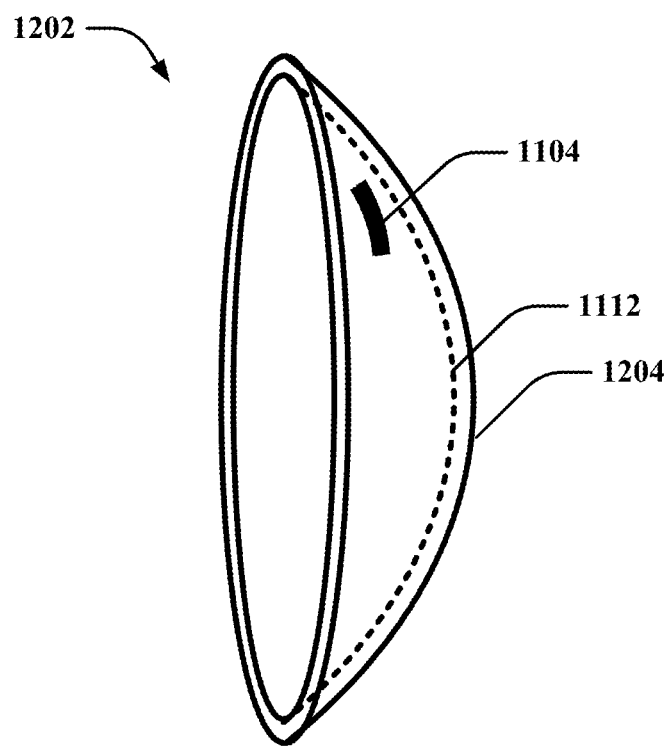
FIG. 12B depicts the final processing of a contact lens form to form a contact lens in accordance with aspects described herein.

FIG. 12B depicts the final processing of contact lens form 1112 to form a contact lens 1202. Contact lens 1202 comprises the contact lens 1112 form embedded and/or coated on one or more sides with contact lens material 1204. In various aspects, the contact lens material 1204 can include one or more of the structure and/or functionality of lens material 216 (and vice versa). For example, in an aspect, the contact lens material 1204 is hydrogel, such as silicone hydrogel. Contact lens 1202 can also include one or more of the structure and/or functionality contact lenses 100, 200, 202, 204 (and vice versa). For example, contact lens 1202 can include contact lens form 1112 entirely embedded in contact lens material 1204 and/or partially covered with contact lens material 1204. In an aspect, in order to form contact lens 1202, contact lens form 1102 is dipped into a liquid contact lens material and then the contact lens material is allowed to solidify.

Figure 13:
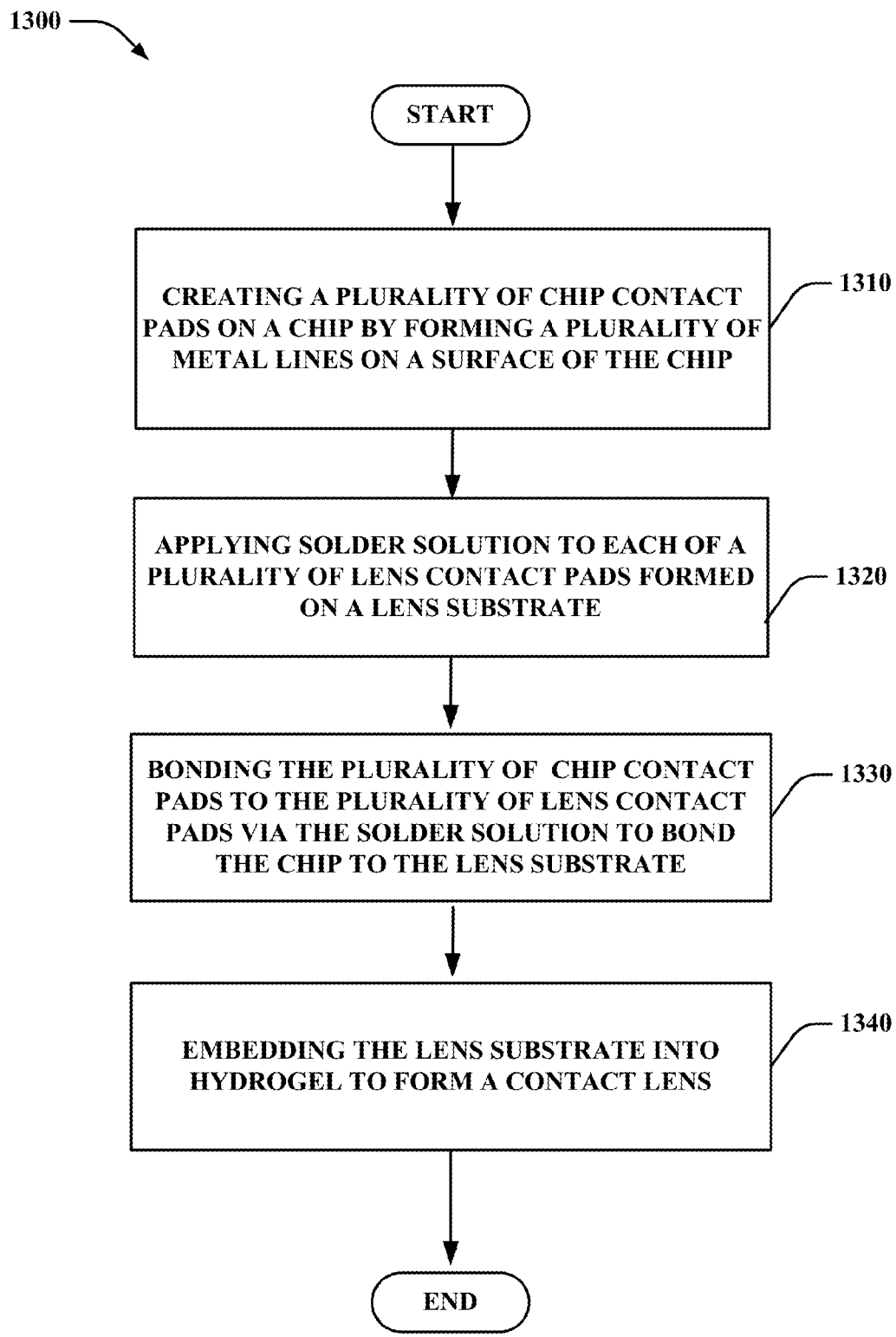
FIG. 13 presents a exemplary methodology by which a silicon chip is assembled onto and/or within a contact lens in accordance with aspects described herein.
Figure 14:
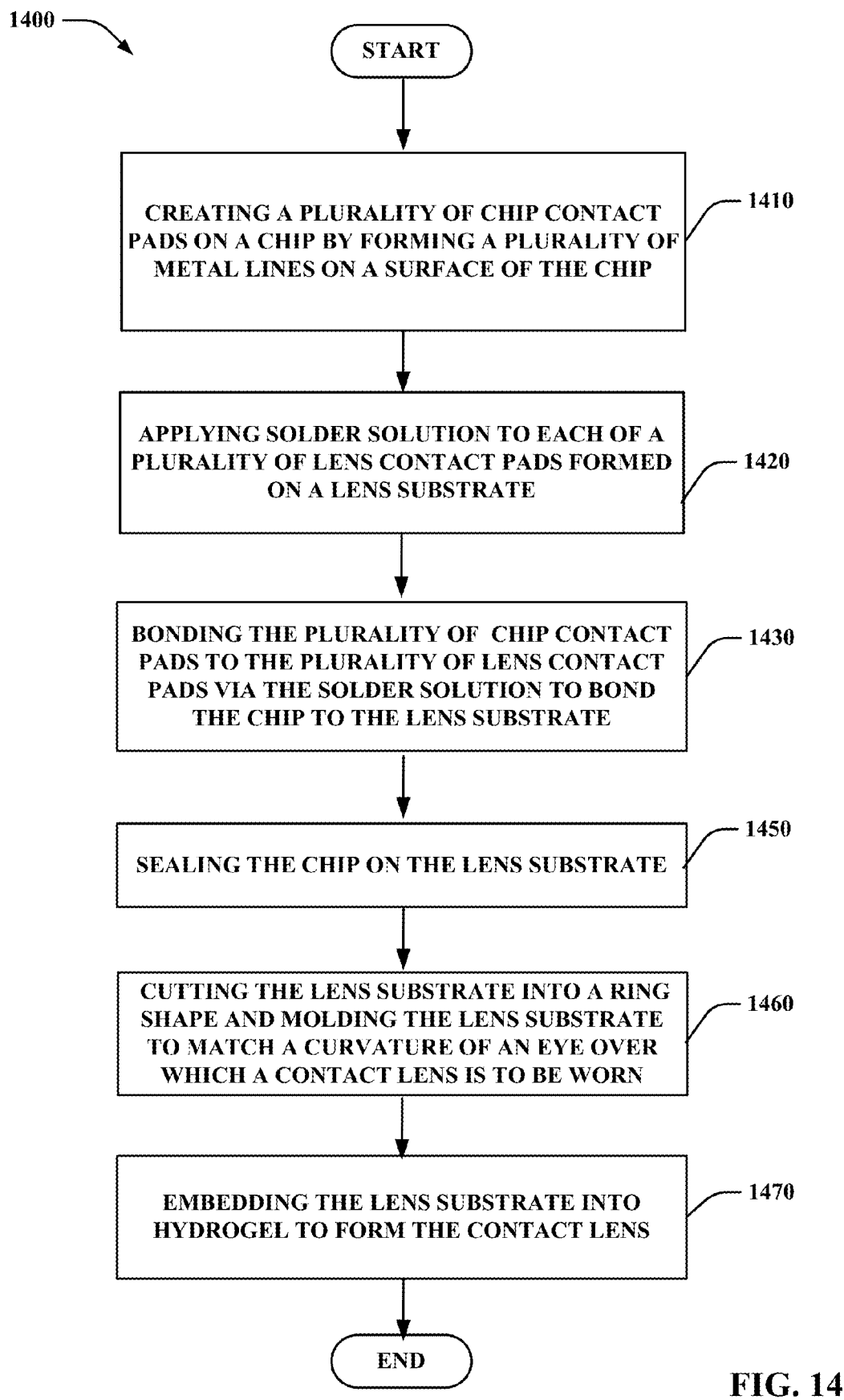
FIG. 14 presents another exemplary methodology by which a silicon chip is assembled onto and/or within a contact lens in accordance with aspects described herein.
Figure 15:
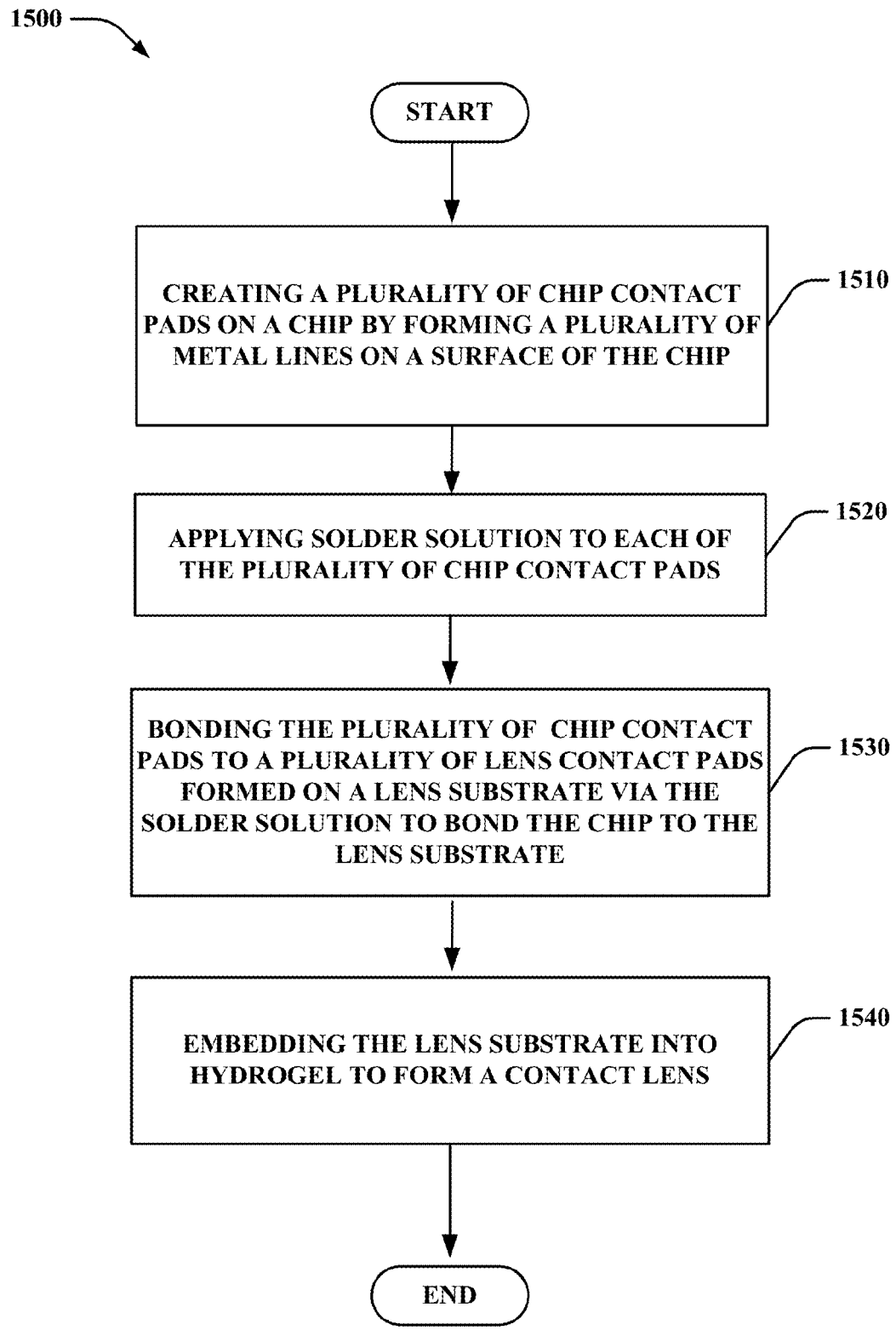
FIG. 15 presents another exemplary methodology by which a silicon chip is assembled onto and/or within a contact lens in accordance with aspects described herein.

FIGS. 13-15 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Referring now to FIG. 13, presented is a flow diagram of an example application of systems and apparatuses disclosed in this description in accordance with an embodiment. In an aspect, in exemplary methodology 1300, a contact lens is formed having a silicon chip integrated therein. At 1310, a plurality of chip contact pads are formed on a chip by forming a plurality of metal lines on a surface of the chip. (e.g. using photolithography). At 1320, solder solution is applied to each of a plurality of lens contact pads formed on a lens substrate (e.g. using a syringe). At 1330, the plurality of chip contact pads are bonded to the plurality of lens contact pads via the solder solution to bond the chip to the lens substrate (e.g. using a flip chip bonder). Then at 1340, the lens substrate is embedded into a hydrogel to form a contact lens.

Referring now to FIG. 14, presented is a flow diagram of another example application of systems and apparatuses disclosed in this description in accordance with an embodiment. In an aspect, in exemplary methodology 1400, a contact lens is formed having a silicon chip integrated therein. At 1410, a plurality of chip contact pads are formed on a chip by forming a plurality of metal lines on a surface of the chip. (e.g. using photolithography). At 1420, solder solution is applied to each of a plurality of lens contact pads formed on a lens substrate (e.g. using a syringe). At 1430, the plurality of chip contact pads are bonded to the plurality of lens contact pads via the solder solution to bond the chip to the lens substrate (e.g. using a flip chip bonder). At 1450, the lens substrate is sealed onto the chip (e.g. using a sealant 1504). At 1460, the lens substrate is cut into a ring shape and molded to match the curvature of an eye over which a contact lens is to be worn. Then at 1340, the lens substrate is embedded into a hydrogel to form the contact lens.

Referring now to FIG. 15, presented is a flow diagram of an example application of systems and apparatuses disclosed in this description in accordance with an embodiment. In an aspect, in exemplary methodology 1500, a contact lens is formed having a silicon chip integrated therein. At 1510, a plurality of chip contact pads are formed on a chip by forming a plurality of metal lines on a surface of the chip. (e.g. using photolithography). At 1520, solder solution is applied to each of the plurality of chip contact pads (e.g. using a syringe). At 1530, the plurality of chip contact pads are bonded to a plurality of lens contact pads via the solder solution to bond the chip to the lens substrate (e.g. using a flip chip bonder). Then at 1540, the lens substrate is embedded into a hydrogel to form a contact lens.

What is claimed is:

1. A method for manufacturing a contact lens having an integrated circuit, comprising:
   creating a plurality of chip contact pads on a chip by forming a grid of metal lines on a surface of the chip, wherein the chip contact pads correspond to intersection points of the metal lines in the grid;
   applying assembly bonding material to each of a plurality of lens contact pads formed on a lens substrate, wherein the assembly bonding material includes an anisotropic conductive material;
   bonding the plurality of chip contact pads to the plurality of lens contact pads via the assembly bonding material to bond the chip to the lens substrate; and
   embedding the lens substrate and the chip bonded thereon into a contact lens material to form the contact lens.

2. The method of claim 1, wherein the forming the grid of metal lines comprises forming the grid of metal lines using photolithography.

3. The method of claim 1, further comprising, prior to the embedding, sealing the chip on the lens substrate.

4. The method of claim 1, further comprising, prior to the embedding, cutting the lens substrate into a ring shape and molding the lens substrate to match a curvature of an eye over which the contact lens is to be worn.

5. The method of claim 1, wherein the chip has a thickness of about 100 microns or less and a length of about 1.0 millimeter or less.

6. The method of claim 1, wherein the contact lens material includes at least one of a hydrogel, a silicone hydrogel or a silicone elastomer.

7. The method of claim 1, wherein the bonding is performed employing a flip-chip bonder.

8. A contact lens having an integrated circuit disposed thereon or therein formed by a process comprising the steps of:
   creating a plurality of chip contact pads on a chip by forming a grid of metal lines on a surface of the chip, wherein the chip contact pads correspond to intersection points of the metal lines in the grid;
   applying assembly bonding material to each of the plurality of chip contact pads, wherein the assembly bonding material includes an anisotropic conductive material;
   bonding the plurality of the chip contact pads to a plurality of lens contact pads formed on a lens substrate via the assembly bonding material to bond the chip to the lens substrate; and
   embedding the lens substrate having the chip bonded thereon into a contact lens material to form the contact lens.

9. The contact lens of claim 8, wherein the step of forming the grid of metal lines comprises forming the grid of metal lines using photolithography.

10. The contact lens of claim 8, wherein the process further comprises the step of, prior to the embedding, sealing the chip on the lens substrate.

11. The contact lens of claim 8, wherein the process further comprises the step of, prior to the embedding, cutting the lens substrate into a ring shape and molding the lens substrate to match a curvature of an eye over which the contact lens is to be worn.

12. The contact lens of claim 8, wherein the chip has a thickness of about 100 microns or less and a length of about 1.0 millimeter or less.

13. The contact lens of claim 8, wherein the bonding is performed employing a flip-chip bonder.

14. The contact lens of claim 8, wherein the contact lens material includes at least one of a hydrogel, a silicone hydrogel or a silicone elastomer.

15. A method for manufacturing a contact lens having an integrated circuit, comprising:
   creating a plurality of lens contact pads on a lens substrate;
   creating a plurality of chip contact pads on a chip, wherein the plurality of chip contact pads corresponding to intersection points of a grid of metal lines on the chip;
   applying assembly bonding material to the each of the plurality of lens contact pads or chip contact pads, wherein the assembly bonding material includes an anisotropic conductive material;

aligning the plurality of lens contact pads with the plurality of chip contact pads;

bonding the chip to the lens substrate via the assembly bonding material using flip chip bonding; and forming a contact lens with the lens substrate.

16. The method of claim 15, wherein the creating the plurality of the lens contact pads comprises forming a respective grid of metal lines on the lens substrate, corresponding to the grid of metal lines on the chip, using photolithography.

17. The method of claim 15, wherein the creating the plurality of the lens contact pads comprises forming a plurality of metal squares, on the lens substrate, having a length of about 100 microns or less.

18. The method of claim 15, wherein the creating the plurality of the chip contact pads comprises forming the grid of metal lines on the chip using photolithography.

19. The method of claim 15, wherein the forming the contact lens comprises:

sealing the chip on the lens substrate;

cutting the lens substrate into a ring shape and molding the lens substrate to match a curvature of an eye over which the contact lens is to be worn; and embedding the lens substrate into a hydrogel.

20. The method of claim 15, wherein the chip has a thickness of about 100 microns or less and a length of about 1.0 millimeter or less.

21. The method of claim 15, wherein the anisotropic conductive material has an activation temperature below 200° C.

* * * * *